(12) United States Patent
Franano et al.

(10) Patent No.: US 9,572,697 B2
(45) Date of Patent: Feb. 21, 2017

(54) BLOCKSTENT DEVICE AND METHODS OF USE

(75) Inventors: F. Nicholas Franano, Olathe, KS (US); Katherine J. Stephenson, Los Gatos, CA (US)

(73) Assignee: Metactive Medical, Inc., Olathe, KS (US)

( * ) Notice: Subject to any disclaimer, the term of this patent is extended or adjusted under 35 U.S.C. 154(b) by 0 days.

(21) Appl. No.: 13/980,274

(22) PCT Filed: Jan. 17, 2012

(86) PCT No.: PCT/US2012/000030
§ 371 (c)(1),
(2), (4) Date: Sep. 27, 2013

(87) PCT Pub. No.: WO2012/099704
PCT Pub. Date: Jul. 26, 2012

(65) Prior Publication Data
US 2014/0018838 A1    Jan. 16, 2014

Related U.S. Application Data

(60) Provisional application No. 61/433,305, filed on Jan. 17, 2011.

(51) Int. Cl.
*A61M 29/00* (2006.01)
*A61F 2/958* (2013.01)
(Continued)

(52) U.S. Cl.
CPC ......... *A61F 2/958* (2013.01); *A61B 17/12031* (2013.01); *A61B 17/12109* (2013.01);
(Continued)

(58) Field of Classification Search
CPC .................... A61B 17/12131; A61B 17/12136;
A61B 17/12031; A61B 17/12109; A61B 2017/00526; A61B 2017/12068; A61B 2019/307; A61B 2017/12054; A61B 2017/01; A61B 2017/12063; A61B 2017/00893; A61M 2025/1054; A61M 25/1029; A61F 2/958; A61F 2/06; Y10T 29/49826
(Continued)

(56) References Cited

U.S. PATENT DOCUMENTS 3,794,268 A * 2/1974 McNeill ................. A22C 13/00
242/160.1
4,311,146 A * 1/1982 Wonder ........... A61B 17/12109
264/264

(Continued)

FOREIGN PATENT DOCUMENTS

CN     1342056 A     3/2002
CN     1813638 A     8/2006
(Continued)

OTHER PUBLICATIONS

International Search Report for PCT/US2012/021621 mailed Aug. 16, 2012 (6 pages).
(Continued)

*Primary Examiner* — Amy R Weisberg
(74) *Attorney, Agent, or Firm* — Polsinelli PC

(57) ABSTRACT

What is disclosed is a medical device comprising a compressed, cylindrical or oblong, thin-walled, expandable metal structure (a "blockstent") and a flexible, elongated device (a "delivery catheter") to position the compressed blockstent into the lumen of a blood vessel segment to be treated, and methods of use for occlusion of treated blood vessel segments. A blockstent can be made with ductile metals such as gold, platinum, or silver such that the blockstent will conform to the shape of the lumen of the treated blood vessel segment during expansion and allow for
(Continued)

the shape of the blockstent to be permanently changed by the application of an external force. The surface of the blockstent can be configured to promote local thrombus on the external surface of the blockstent and to promote the growth of tissue into the wall of the blockstent in order to occlude the treated blood vessel and fix the blockstent in place. The wall of the blockstent can also be configured to release drugs or pharmacologically active molecules such as those that promote thrombosis, cell proliferation, extracellular matrix deposition to promote this thrombus formation and tissue growth.

39 Claims, 20 Drawing Sheets

(51) Int. Cl.
  *A61B 17/12* (2006.01)
  *A61F 2/06* (2013.01)
  *A61M 25/10* (2013.01)
  *A61B 17/00* (2006.01)

(52) U.S. Cl.
  CPC .. *A61B 17/12131* (2013.01); *A61B 17/12136* (2013.01); *A61F 2/06* (2013.01); *A61M 25/1029* (2013.01); *A61B 2017/00526* (2013.01); *A61B 2017/00893* (2013.01); *A61B 2017/12054* (2013.01); *A61B 2017/12059* (2013.01); *A61B 2017/12063* (2013.01); *A61B 2017/12068* (2013.01); *A61B 2090/037* (2016.02); *Y10T 29/49826* (2015.01)

(58) Field of Classification Search
  USPC ........ 604/96.01–105; 606/191, 200, 95, 213, 606/195; 623/1.25, 1.28–1.29
  See application file for complete search history.

(56) References Cited

U.S. PATENT DOCUMENTS

| | | | |
|---|---|---|---|
| 4,341,218 A | 7/1982 | Ü | |
| 4,364,392 A * | 12/1982 | Strother | A61B 17/0057 604/103.01 |
| 4,395,806 A * | 8/1983 | Wonder | A61B 17/12109 29/424 |
| 4,402,319 A | 9/1983 | Handa et al. | |
| 4,416,028 A | 11/1983 | Eriksson et al. | |
| 4,471,779 A * | 9/1984 | Antoshkiw | A61B 17/12109 604/907 |
| 4,517,979 A * | 5/1985 | Pecenka | A61B 17/12109 604/907 |
| 4,638,803 A * | 1/1987 | Rand | A61B 17/12136 604/175 |
| 4,770,067 A * | 9/1988 | Liu | B23P 15/40 76/104.1 |
| 4,819,637 A * | 4/1989 | Dormandy, Jr. | A61B 17/12113 137/846 |
| 5,041,090 A | 8/1991 | Scheglov et al. | |
| 5,167,627 A | 12/1992 | Clegg et al. | |
| 5,181,921 A * | 1/1993 | Makita | A61B 17/12109 604/247 |
| 5,222,970 A | 6/1993 | Reeves | |
| 5,282,847 A * | 2/1994 | Trescony | A61F 2/06 623/1.29 |
| 5,327,885 A | 7/1994 | Griffith | |
| 5,344,401 A | 9/1994 | Radisch et al. | |
| 5,354,295 A | 10/1994 | Guglielmi et al. | |
| 5,370,691 A | 12/1994 | Samson | |
| 5,382,261 A | 1/1995 | Palmaz | |
| 5,522,836 A | 6/1996 | Palermo | |
| 5,609,606 A * | 3/1997 | O'Boyle | A61B 17/2202 604/22 |
| 5,769,817 A | 6/1998 | Burgmeier | |
| 5,833,671 A | 11/1998 | Macoviak et al. | |
| 6,022,359 A | 2/2000 | Frantzen | |
| 6,063,070 A | 5/2000 | Eder | |
| 6,096,021 A | 8/2000 | Helm et al. | |
| 6,146,372 A | 11/2000 | Leschinsky et al. | |
| 6,156,005 A | 12/2000 | Theron | |
| 6,186,978 B1 * | 2/2001 | Samson | A61M 25/005 604/525 |
| 6,293,960 B1 | 9/2001 | Ken | |
| 6,293,968 B1 | 9/2001 | Taheri | |
| 6,312,405 B1 | 11/2001 | Meyer et al. | |
| 6,344,041 B1 | 2/2002 | Kupiecki et al. | |
| 6,346,117 B1 | 2/2002 | Greenhalgh | |
| 6,395,008 B1 | 5/2002 | Ellis et al. | |
| 6,425,893 B1 | 7/2002 | Guglielmi | |
| 6,454,780 B1 | 9/2002 | Wallace | |
| 6,463,317 B1 | 10/2002 | Kucharczyk et al. | |
| 6,676,667 B2 | 1/2004 | Mareiro et al. | |
| 6,706,064 B1 * | 3/2004 | Anson | A61B 17/12109 623/1.1 |
| 6,733,513 B2 | 5/2004 | Boyle et al. | |
| 6,976,950 B2 * | 12/2005 | Connors | A61F 2/0027 600/29 |
| 6,976,951 B2 * | 12/2005 | Connors | A61F 2/0027 600/29 |
| 7,329,236 B2 * | 2/2008 | Kesten | A61M 25/1002 604/96.01 |
| 7,410,482 B2 | 8/2008 | Murphy et al. | |
| 7,527,622 B2 | 5/2009 | Lane et al. | |
| 7,632,291 B2 * | 12/2009 | Stephens | A61B 17/12022 606/195 |
| 7,632,301 B2 | 12/2009 | Alt | |
| 7,713,297 B2 | 5/2010 | Alt | |
| 7,955,246 B2 | 6/2011 | Lubock et al. | |
| 8,007,674 B2 | 8/2011 | Johnson | |
| 8,016,853 B2 | 9/2011 | Griffen et al. | |
| 8,333,798 B2 | 12/2012 | Gandhi et al. | |
| 8,372,114 B2 | 2/2013 | Hines | |
| 8,574,146 B2 * | 11/2013 | Gillespie, Jr. | A61B 90/02 600/30 |
| 8,668,717 B2 | 3/2014 | Hines | |
| 9,283,100 B2 * | 3/2016 | Wang | A61F 2/958 |
| 2002/0016624 A1 * | 2/2002 | Patterson et al. | 623/1.12 |
| 2002/0082638 A1 * | 6/2002 | Porter | A61B 17/12113 606/195 |
| 2002/0143383 A1 | 10/2002 | Parodi | |
| 2002/0169473 A1 | 11/2002 | Septka et al. | |
| 2003/0028210 A1 | 2/2003 | Boyle et al. | |
| 2003/0074039 A1 | 4/2003 | Puskas | |
| 2003/0083732 A1 | 5/2003 | Stinson | |
| 2003/0171739 A1 | 9/2003 | Murphy et al. | |
| 2003/0212419 A1 | 11/2003 | West | |
| 2003/0236494 A1 | 12/2003 | Seward | |
| 2004/0138733 A1 | 7/2004 | Weber et al. | |
| 2004/0236278 A1 | 11/2004 | Herweck et al. | |
| 2004/0254625 A1 | 12/2004 | Stephens et al. | |
| 2005/0033408 A1 | 2/2005 | Jones et al. | |
| 2005/0090888 A1 | 4/2005 | Hines et al. | |
| 2005/0136090 A1 | 6/2005 | Falotico et al. | |
| 2005/0171593 A1 | 8/2005 | Whirley et al. | |
| 2006/0015169 A1 | 1/2006 | Letort | |
| 2006/0079923 A1 * | 4/2006 | Chhabra | A61B 17/12113 606/192 |
| 2006/0085070 A1 * | 4/2006 | Kim | A61B 17/7065 623/17.11 |
| 2006/0135947 A1 | 6/2006 | Soltesz et al. | |
| 2006/0155296 A1 * | 7/2006 | Richter | 606/94 |
| 2006/0155364 A1 | 7/2006 | Holloway et al. | |
| 2006/0200191 A1 | 9/2006 | Zadno-Azizi | |
| 2007/0032854 A1 | 2/2007 | Schmid et al. | |
| 2007/0129746 A1 | 6/2007 | Mische | |
| 2007/0150041 A1 | 6/2007 | Evans et al. | |
| 2007/0239191 A1 * | 10/2007 | Ramzipoor | A61B 17/12022 606/191 |
| 2007/0244431 A1 | 10/2007 | Limon | |
| 2007/0265656 A1 | 11/2007 | Amplatz et al. | |
| 2007/0267780 A1 | 11/2007 | Schewe et al. | |

(56) References Cited

U.S. PATENT DOCUMENTS

| | | | |
|---|---|---|---|
| 2007/0288083 | A1 | 12/2007 | Hines |
| 2007/0299422 | A1* | 12/2007 | Inganas ............... A61B 17/0057 604/508 |
| 2007/0299460 | A9* | 12/2007 | Boucher ................ A61B 17/68 606/191 |
| 2008/0188825 | A1 | 8/2008 | Atanasoska et al. |
| 2008/0195112 | A1* | 8/2008 | Liu .................... A61B 17/8858 606/92 |
| 2008/0281350 | A1 | 11/2008 | Sepetka et al. |
| 2008/0294205 | A1* | 11/2008 | Greenhalgh ............ A61F 2/958 606/86 A |
| 2009/0062726 | A1 | 3/2009 | Ford et al. |
| 2009/0287297 | A1 | 11/2009 | Cox |
| 2010/0096320 | A1 | 4/2010 | Opperman |
| 2010/0114299 | A1 | 5/2010 | Ben Muvhar et al. |
| 2010/0174353 | A1 | 7/2010 | Kantor |
| 2010/0198336 | A1 | 8/2010 | Weber et al. |
| 2010/0222803 | A1 | 9/2010 | Seifert et al. |
| 2010/0241178 | A1* | 9/2010 | Tilson ................ A61B 17/8816 606/86 R |
| 2010/0312179 | A1 | 12/2010 | Nikolchev et al. |
| 2010/0324649 | A1 | 12/2010 | Mattsson et al. |
| 2011/0046658 | A1 | 2/2011 | Connor et al. |
| 2011/0190776 | A1* | 8/2011 | Palmaz ............... A61B 17/7097 606/92 |
| 2011/0213403 | A1 | 9/2011 | Aboytes |
| 2012/0009325 | A1 | 1/2012 | Storment |
| 2012/0283768 | A1 | 11/2012 | Cox et al. |
| 2012/0296407 | A1 | 11/2012 | Caselnova |
| 2012/0330348 | A1 | 12/2012 | Strauss et al. |
| 2014/0012307 | A1* | 1/2014 | Franano et al. ............. 606/195 |
| 2014/0012363 | A1* | 1/2014 | Franano et al. ............. 623/1.12 |
| 2014/0018838 | A1* | 1/2014 | Franano et al. ............. 606/195 |
| 2015/0005804 | A1* | 1/2015 | Franano ........... A61B 17/12113 606/195 |
| 2016/0030050 | A1 | 2/2016 | Franano et al. |

FOREIGN PATENT DOCUMENTS

| | | |
|---|---|---|
| CN | 101843949 A | 9/2010 |
| EP | 0 101 012 A2 | 2/1984 |
| JP | 2007236472 A | 9/2007 |
| JP | 2009521287 A | 6/2009 |
| NO | 99/03404 A1 | 1/1999 |
| NO | 2004/112656 A2 | 12/2004 |
| NO | 2009/045764 A1 | 4/2009 |
| WO | 99/60932 A1 | 12/1999 |
| WO | 00/27292 A1 | 5/2000 |
| WO | 02/38038 A2 | 5/2002 |
| WO | 02/051320 A2 | 7/2002 |
| WO | 02/087449 A1 | 11/2002 |
| WO | 03/011363 A2 | 2/2003 |
| WO | 03/061528 A1 | 7/2003 |
| WO | 2006/074410 A2 | 7/2006 |
| WO | 2007/006139 A1 | 1/2007 |
| WO | 2007/092103 A2 | 8/2007 |
| WO | 2009/134337 A1 | 11/2009 |
| WO | 2009/135166 A2 | 11/2009 |
| WO | 2010/028310 A2 | 3/2010 |
| WO | 2012/099704 A2 | 7/2012 |
| WO | 2012/099909 A2 | 7/2012 |
| WO | 2012 099910 A2 | 7/2012 |
| WO | 2013/109309 A1 | 7/2013 |
| WO | 2014/146001 A2 | 9/2014 |
| WO | 2016/044647 A2 | 3/2016 |

OTHER PUBLICATIONS

Written Opinion for PCT/US2012/021621 mailed Aug. 16, 2012 (20 pages).
International Search Report for PCT/US2012/021620 mailed Aug. 3, 2012 (5 pages).
Written Opinion for PCT/US2012/021620 mailed Aug. 3, 2012 (13 pages).
European Extended Search Report; Application No. 12736799.3 dated Oct. 2, 2014 (12 pages).
International Search Report PCT/US2012/000030 (WO 2012/099704 A3) mailed Aug. 7, 2012 (4 pages).
Extended European Search Report from related European Application No. 12736401.6, dated Oct. 2, 2014; 11 pgs.
Extended European Search Report from related European Application No. 12737004.7, dated Oct. 2, 2014; 12 pgs.
Extended European Search Report from related European Application No. 12865636.0, dated Aug. 6, 2015; 10 pgs.
International Search Report and Written Opinion from related International Application No. PCT/US2012/047072, dated Dec. 20, 2012; 26 pgs.
International Search Report and Written Opinion from related International Application No. PCT/US2014/030869, dated Nov. 7, 2014; 26 pgs.
Office Action from related Australian Patent Application No. 2012207386, dated Nov. 14, 2015; 3 pgs.
Office Action from related Australian Patent Application No. 2012207387, dated Jan. 21, 2016; 2 pgs.
Office Action from related Australian Patent Application No. 2012207618, dated Jan. 22, 2016; 2 pgs.
First Office Action from related Chinese Patent Application No. 201280005574.7, dated Nov. 21, 2014; 8 pgs.
Second Office Action and Search Report from related Chinese Patent Application No. 201280005574.7, dated Jun. 30, 2015; 21 pgs.
Third Office Action from related Chinese Patent Application No. 201280005574.7, dated Jan. 19, 2016; 7 pgs.
First Office Action and Search Report from related Chinese Patent Application No. 201280005586.X, dated Dec. 2, 2015; 13 pgs.
First Office Action and Search Report from related Chinese Patent Application No. 201280008971.X, dated Aug. 21, 2015; 16 pgs.
Office Action from related Japanese Application No. 2013-549436, dated Nov. 17, 2015; 13 pgs.
Office Action from related Japanese Application No. 2013-549618, dated Nov. 17, 2015; 12 pgs.
Office Action from related Japanese Application No. 2013-549617, dated Nov. 17, 2015; 7 pgs.
Office Action from related Russian Application No. 2013128987, dated Feb. 17, 2016; 13 pgs.
Office Action from related Russian Patent Application No. 2013138347, dated Dec. 30, 2015; 15 pgs.
Office Action from related Russian Application No. 2013138406, dated Jan. 13, 2016; 15 pgs.
Office Action from related U.S. Appl. No. 13/980,278, dated Oct. 23, 2015; 27 pgs.
Office Action from related U.S. Appl. No. 13/980,276, dated Feb. 25, 2016; 22 pgs.
Office Action from related U.S. Appl. No. 13/980,276, dated Jun. 1, 2015; 17 pgs.
Office Action from related U.S. Appl. No. 13/980,276, dated Sep. 5, 2014; 10 pgs.
International Search Report and Written Opinion from related International Application No. PCT/US2015/050783, dated Apr. 11, 2016; 15 pgs.
Office Action from related Japanese Application No. 2013-549436, dated Nov. 8, 2016; 10 pgs.
Office Action from related Japanese Application No. 2013-549618, dated Nov. 8, 2016; 9 pgs.
Office Action from related Japanese Application No. 2013-549617, dated Nov. 8, 2016; 8 pgs.
Second Office Action from related Chinese Patent Application No. 201280008971.X, dated Jul. 5, 2016; 3 pgs.
Fourth Office Action from related Chinese Patent Application No. 201280005574.7, dated May 25, 2016; 3 pgs.
Office Action from related Israeli Patent Application No. 227465, dated Oct. 25, 2016; 4 pgs.
Second Office Action from related Chinese Patent Application No. 201280005586.X, dated Oct. 19, 2016; 7 pgs.

(56) References Cited

OTHER PUBLICATIONS

Office Action from related U.S. Appl. No. 13/980,278, dated Aug. 5, 2016; 33 pgs.
Office Action from related Russian Patent Application No. 2013138347, dated Apr. 5, 2016; 25 pgs.
Office Action from related Israeli Patent Application No. 227439, dated Oct. 11, 2016; 4 pgs.
Office Action from related Russian Patent Application No. 2013138406, dated May 12, 2016; 24 pgs.
Office Action from related Israeli Patent Application No. 227440, dated Oct. 6, 2016; 4 pgs.
Office Action from related Russian Patent Application No. 2013128987, dated May 25, 2016; 6 pgs.
Office Action from related Japanese Patent Application No. 2014-552181, dated Jul. 5, 2016; 4 pgs.
Office Action from related U.S. Appl. No. 14/372,967, dated Nov. 14, 2016; 19 pgs.
Office Action from related Russian Patent Application No. 2014133717, dated Jun. 27, 2016; 5 pgs.
Office Action from related Russian Patent Application No. 2015144196, dated Jun. 15, 2016; 1 pg.

\* cited by examiner

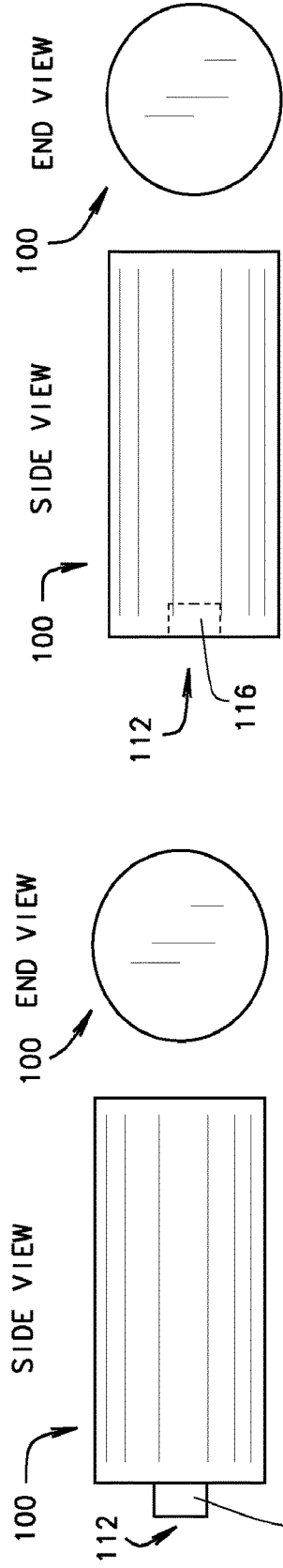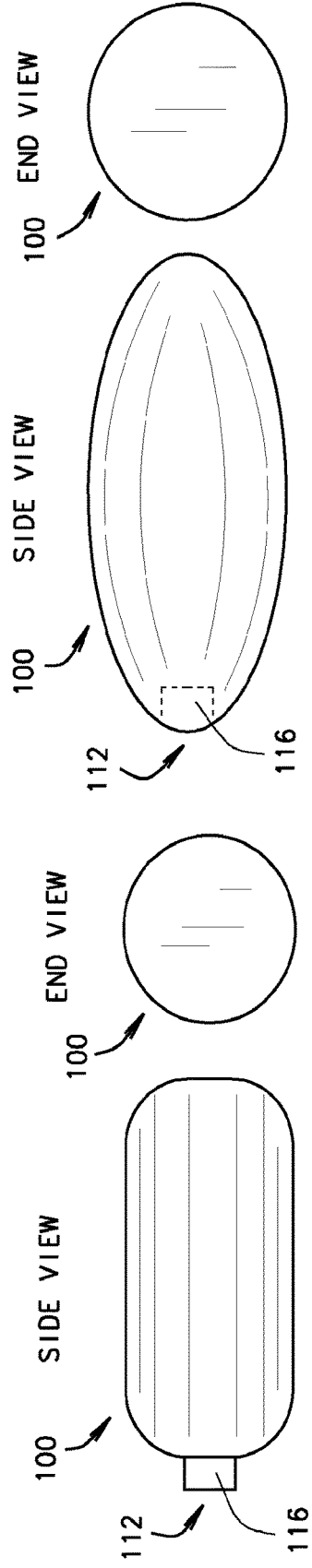

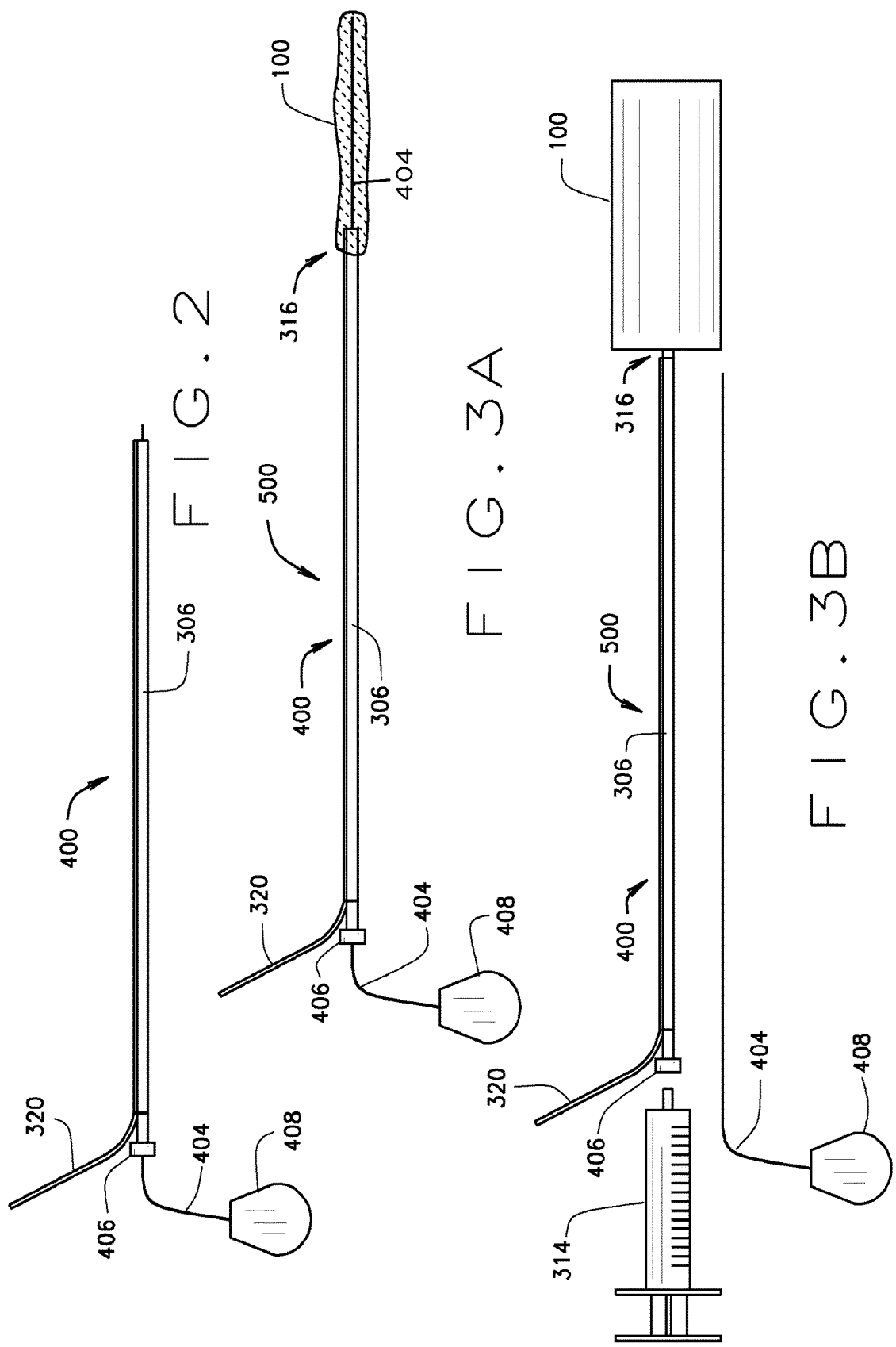

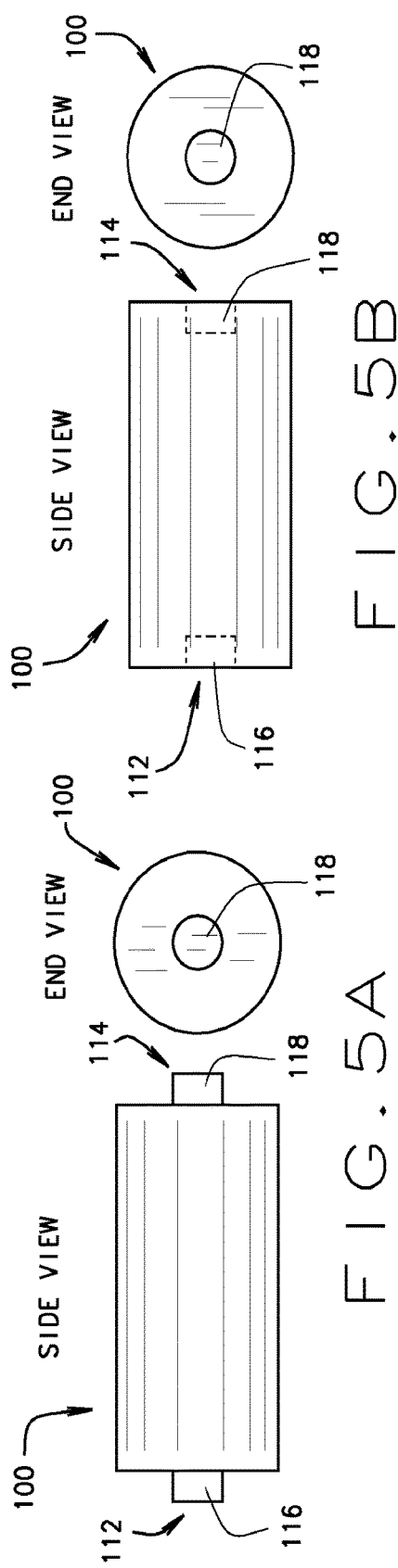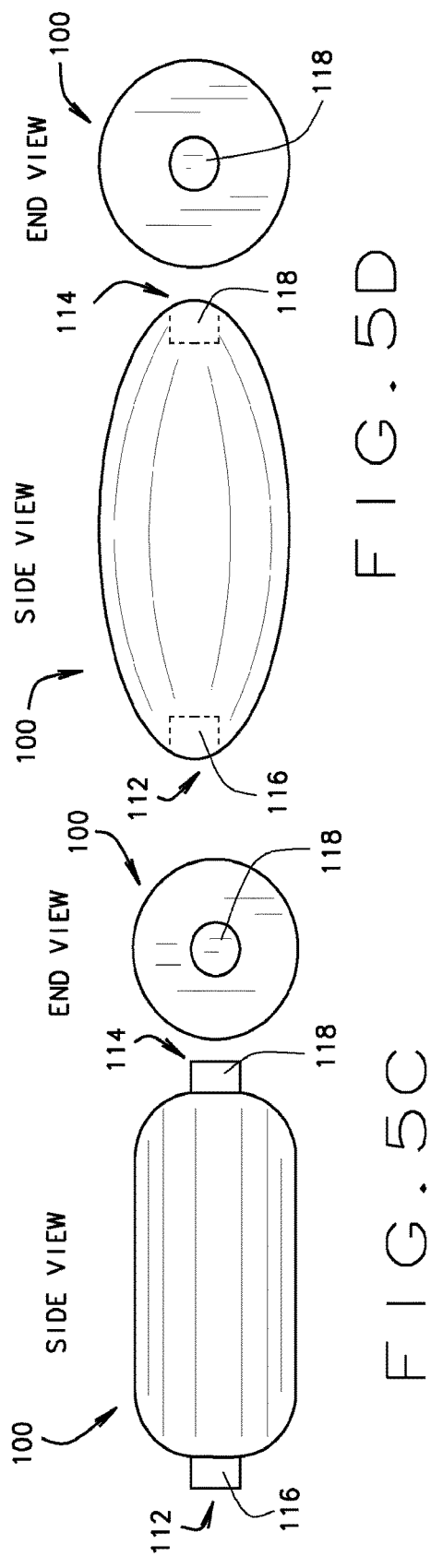

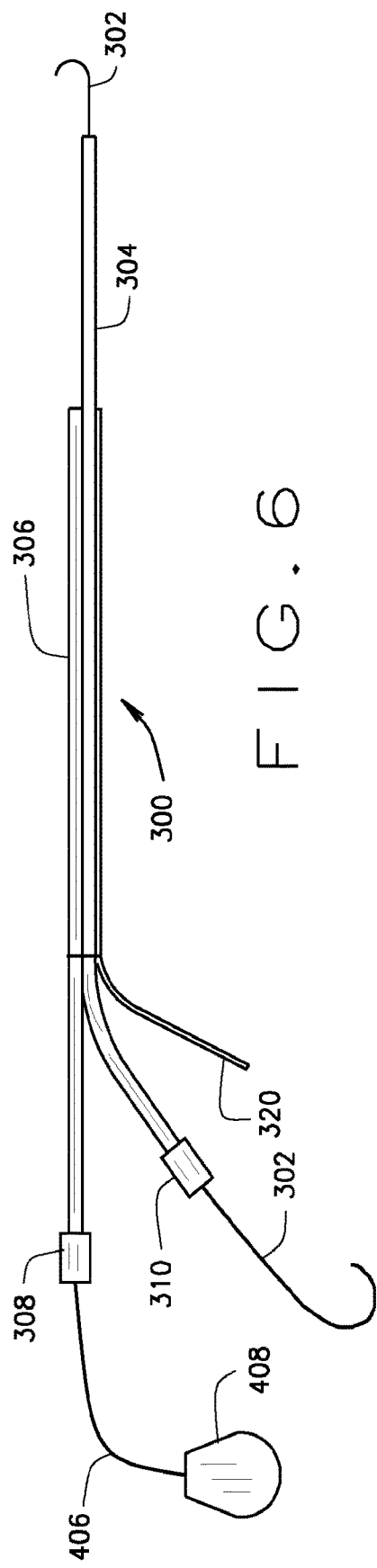

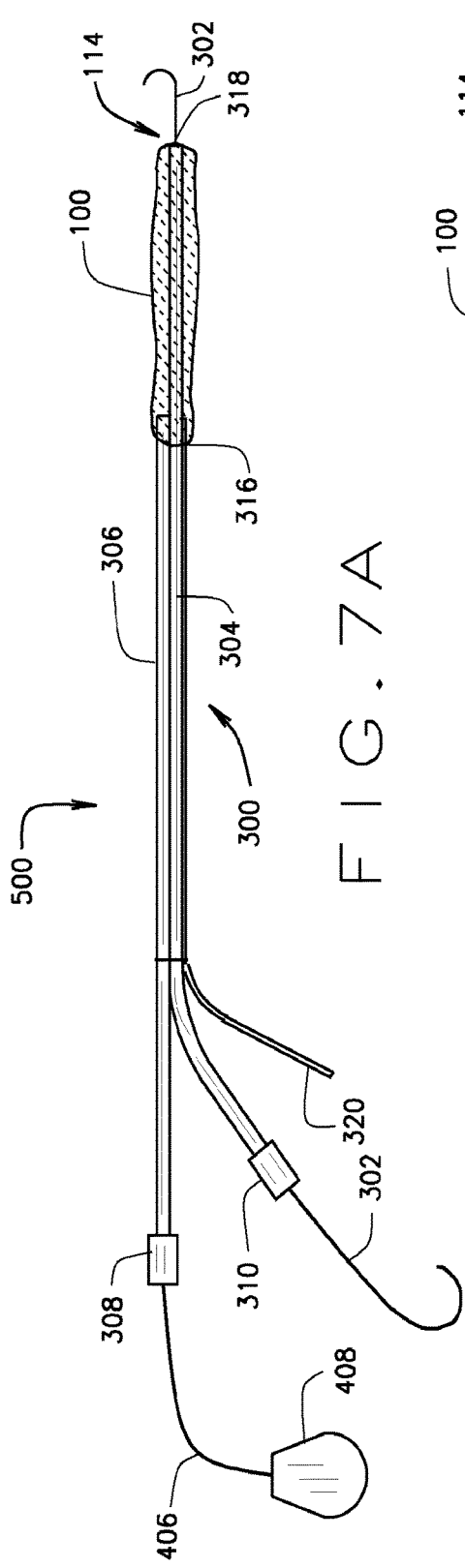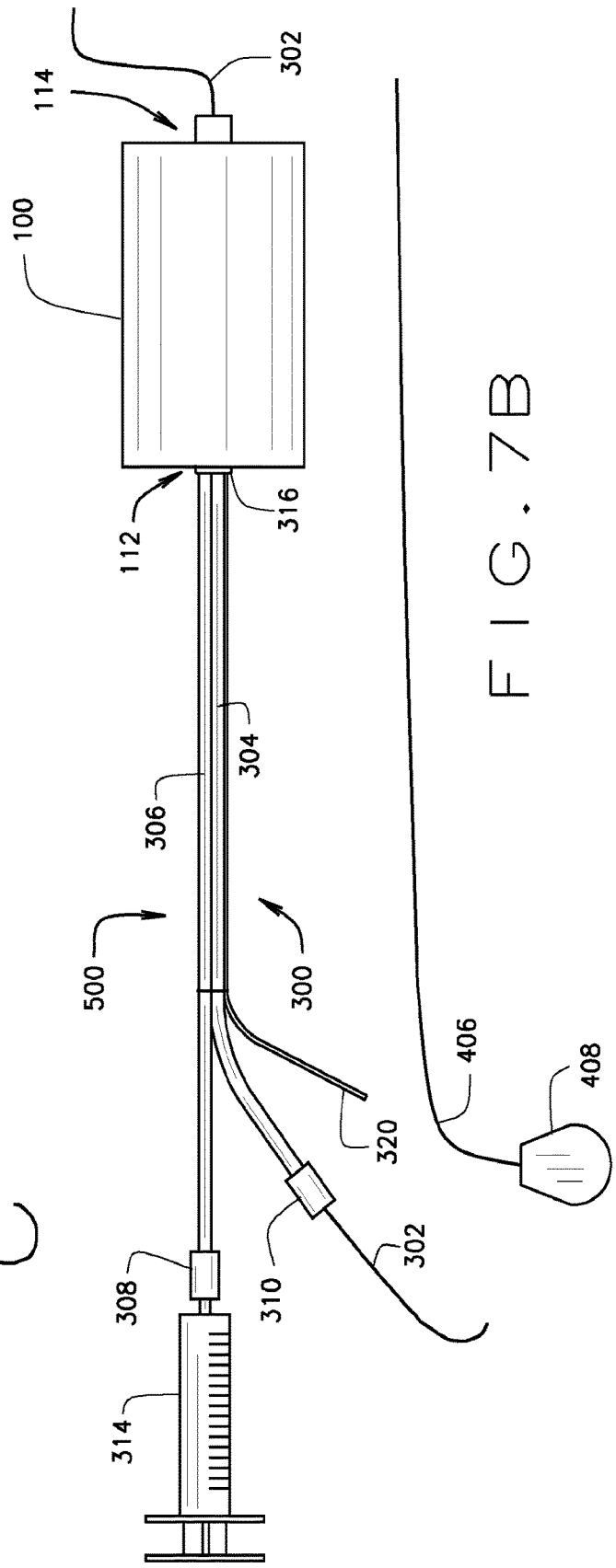

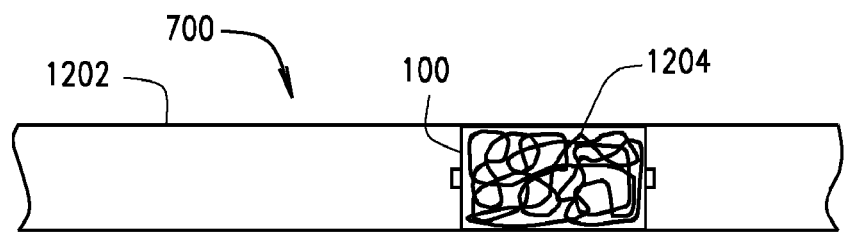
F I G . 1 0
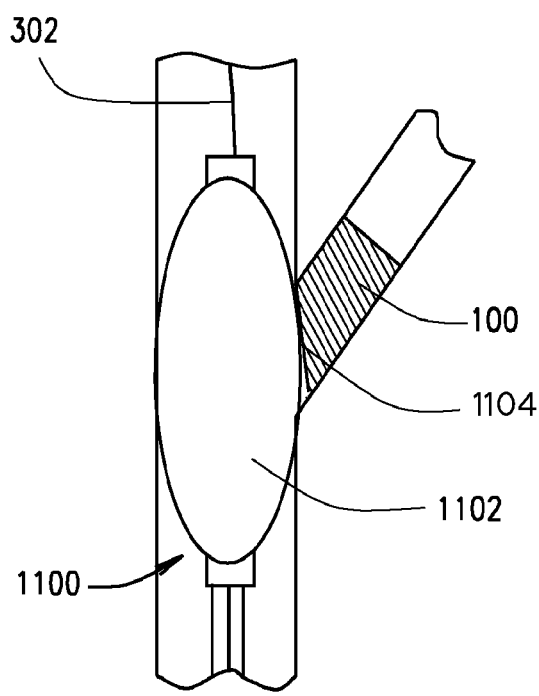
F I G . 1 1
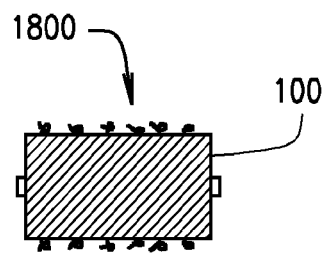
F I G . 1 2 A
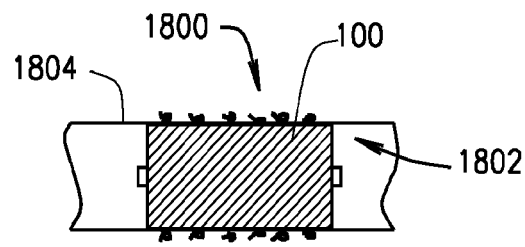
F I G . 1 2 B

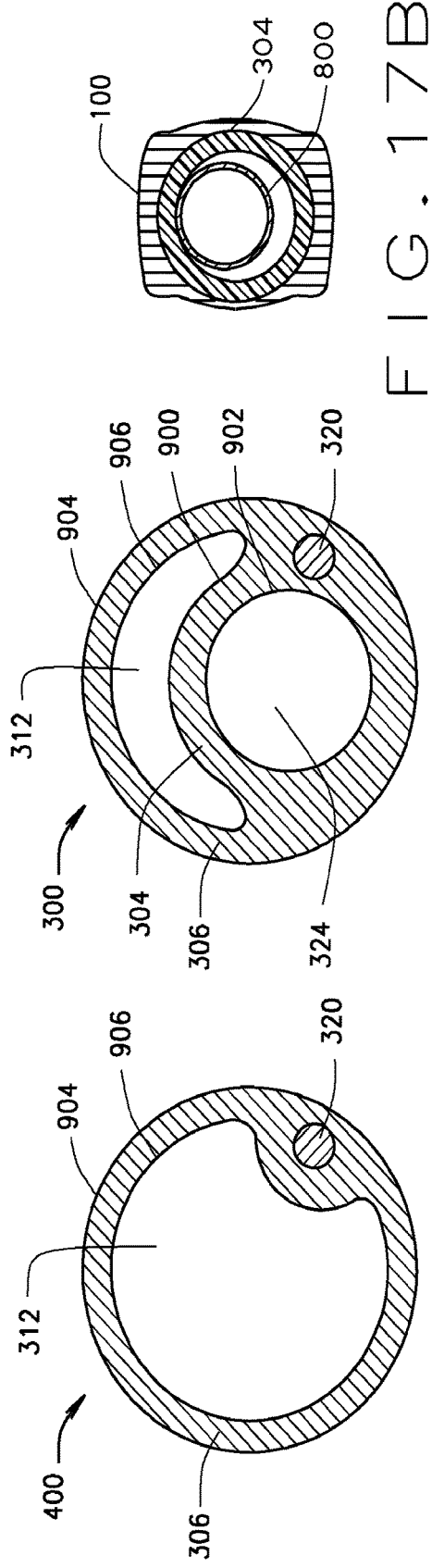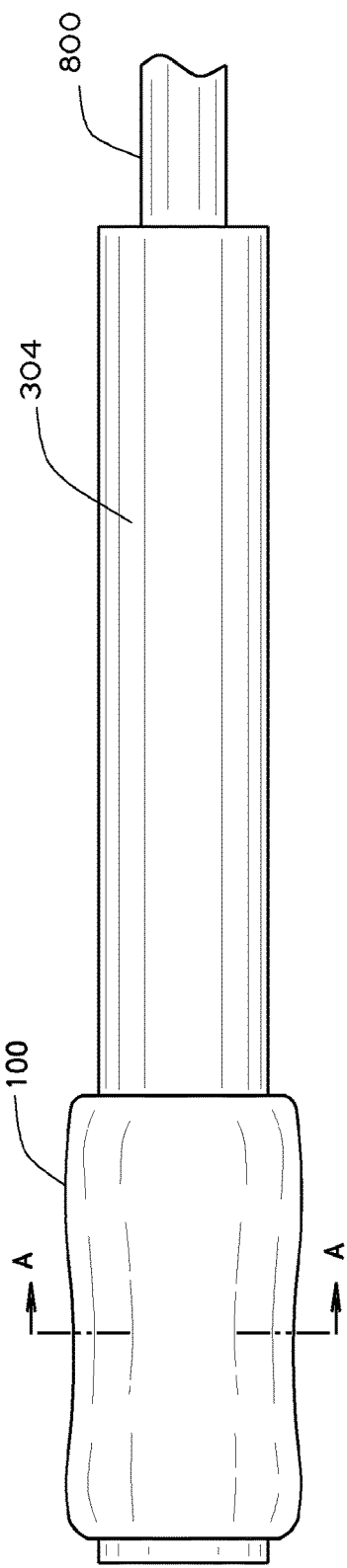
FIG. 16A
FIG. 16B
FIG. 17A
FIG. 17B

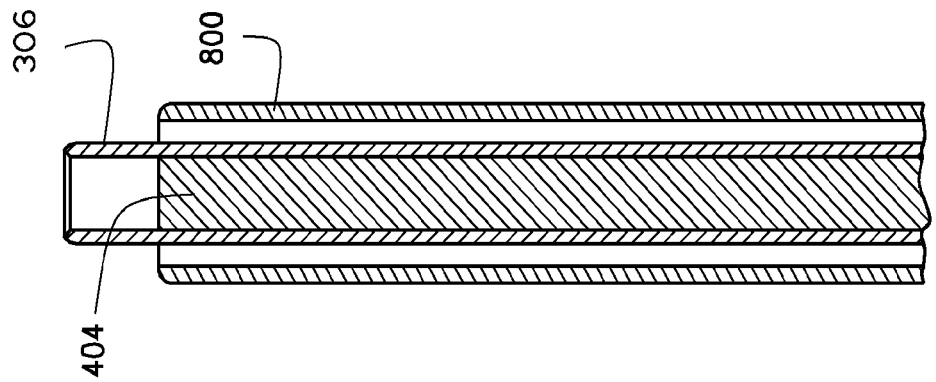
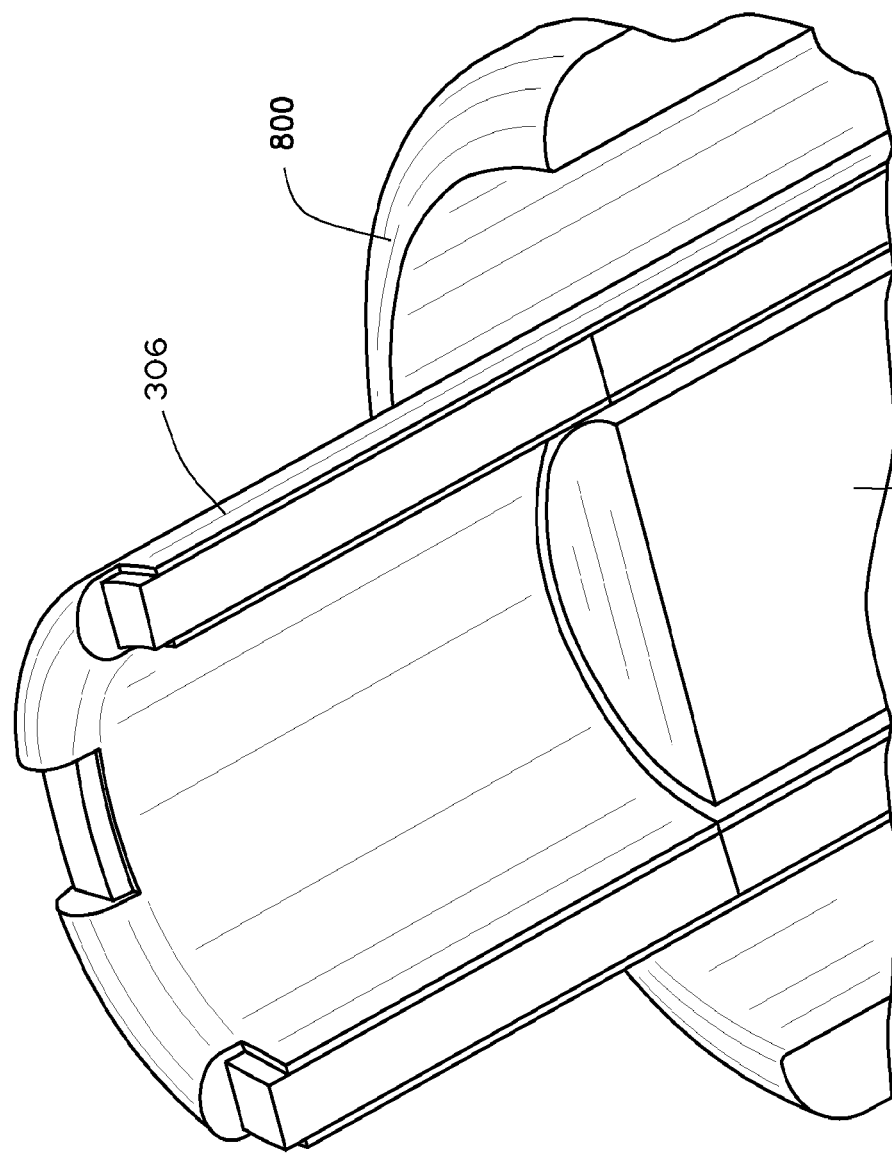

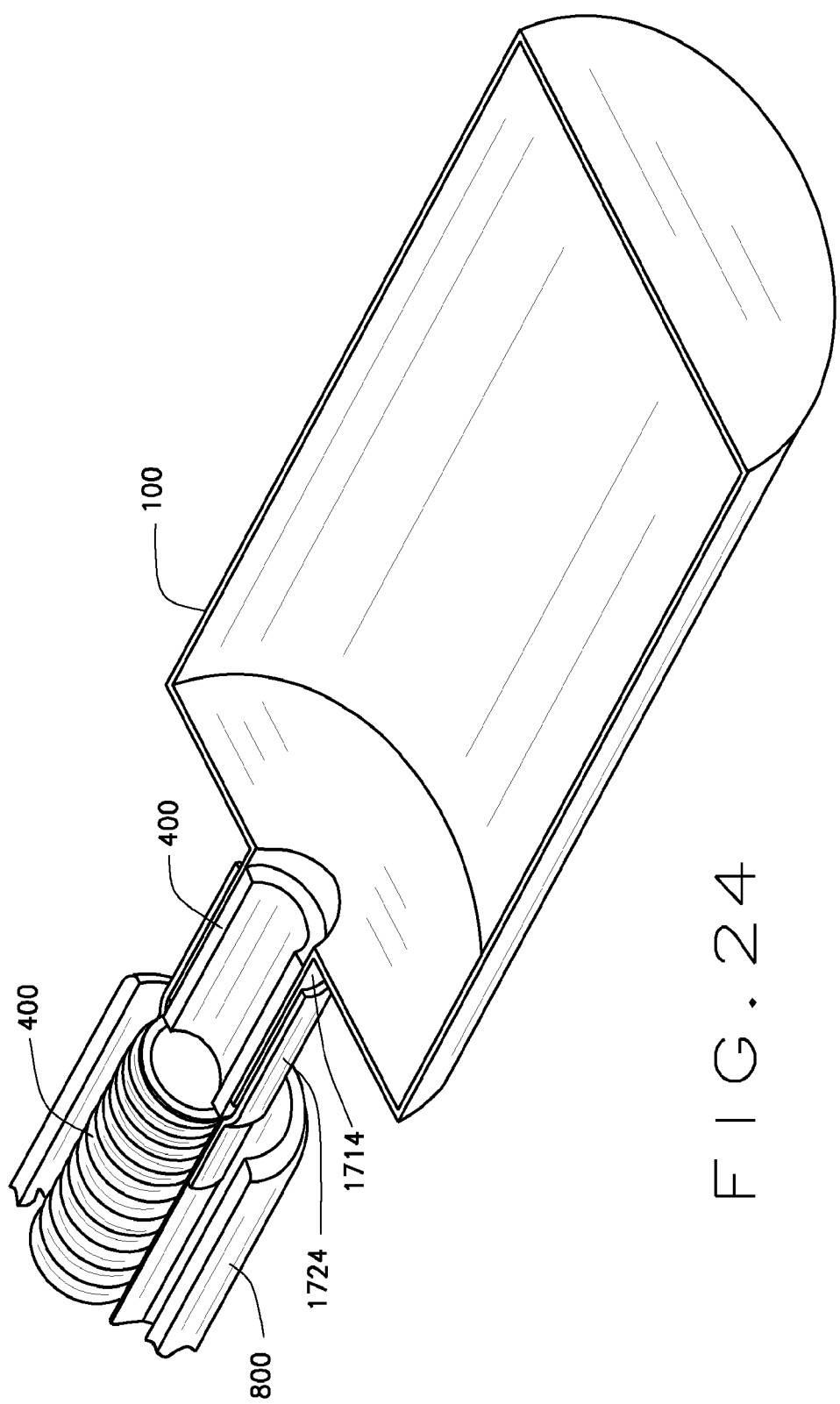

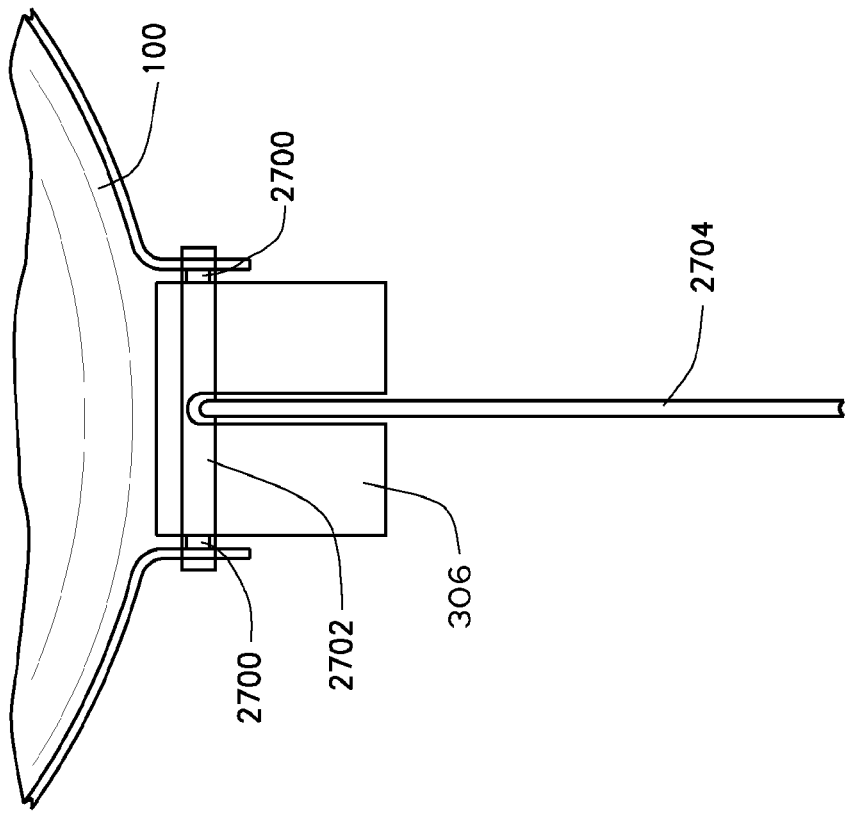
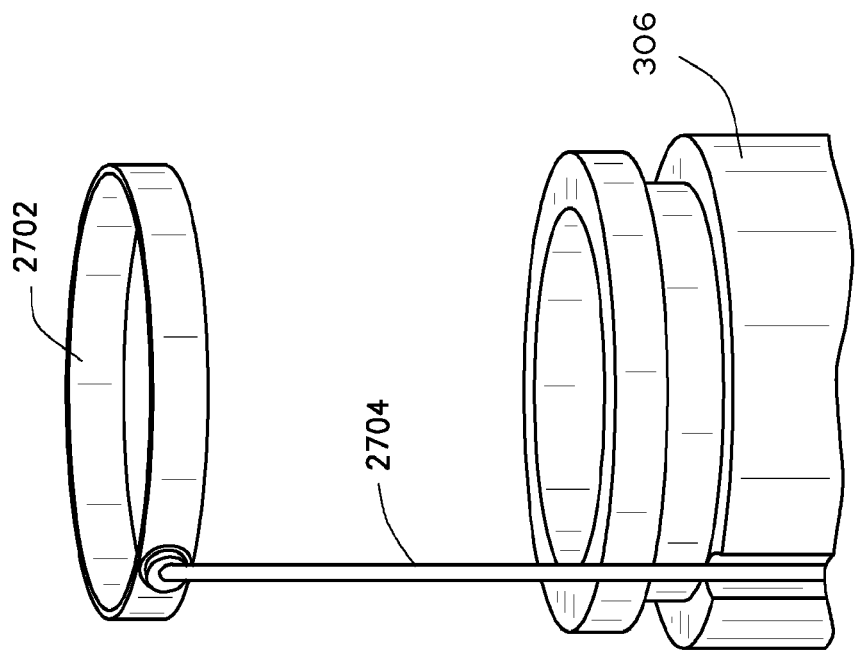

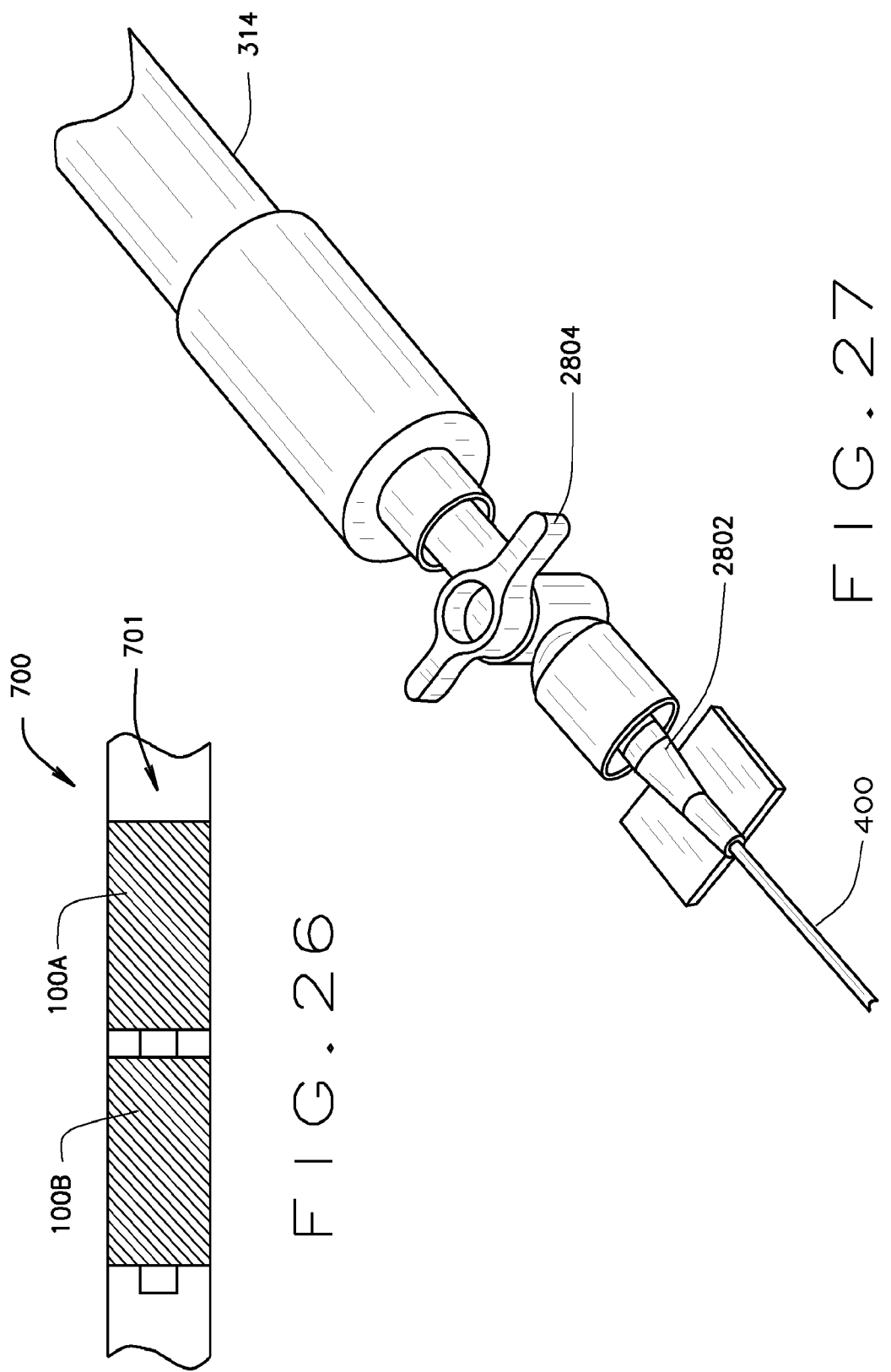

BLOCKSTENT DEVICE AND METHODS OF USE

CROSS REFERENCE TO RELATED APPLICATIONS

This application is a U.S. National Patent Application of PCT/US2012/000030 filed Jan. 17, 2012, which claims the benefit of U.S. Provisional Patent Application No. 61/433,305 filed Jan. 17, 2011, the disclosure of which is incorporated herein by reference in their entirety for all purposes.

FIELD OF THE PRESENT DISCLOSURE

The present disclosure relates to a medical device comprising a blockstent and a delivery catheter for the treatment of blood vessel segments of the vascular system. The present disclosure also relates to various forms of blockstents and delivery catheters, and methods of their manufacture. The present disclosure further relates to methods of occluding blood vessel segments using the various medical devices, whereby the blockstent ultimately remains in the blood vessel segment. Blockstents are cylindrical, thin-walled expandable metal structures comprised of a stent-like device and designed to fill the lumen of a blood vessel segment. Blockstents are configured for: attachment to delivery catheters, compression, advancement through the vascular system, expansion within lumen of blood vessel segments, and then separation from delivery catheters. Delivery catheters of various sizes, shapes, materials, and configurations can be used to position a compressed blockstent in a blood vessel segment and expand the blockstent in the blood vessel by the passage of fluids or solids through the delivery catheter and into the central void or space of the blockstent. Further, the invention relates to components for, and methods of, attaching the blockstent to the delivery catheter, as well as components for, and methods of, separating the expanded blockstent from the delivery catheter, such that the blockstent remains in place in an expanded state within the blood vessel while the delivery catheter is removed from the body.

BACKGROUND OF THE PRESENT DISCLOSURE

In certain clinical situations, patients can benefit from the occlusion of certain artery or vein segments through endovascular means. Clinical settings where endovascular vessel occlusion is beneficial include reducing bleeding from an injured vessel, reducing blood flow to tumors, and rerouting the path of blood in the vascular system for other purposes. Alternatively, minimally invasive, catheter-based, endovascular treatments have been developed to occlude blood vessel segments. Endovascular medical devices for blood vessel occlusion include balloon catheters wherein the balloon can be inflated to fill the lumen of a blood vessel segment and detached from the catheter. There are two major drawbacks to the use of detachable balloon catheters for blood vessel occlusion. First, the balloons are made of polymers that generally resist tissue incorporation that limits fixation of the devices where they are placed. Second, the balloons are configured with elastic walls which are expanded with pressurization and valves designed to maintain that pressure after detachment. Unfortunately, there is a substantial rate of balloon and valve failure, resulting in deflation. Without tissue incorporation, balloon deflation can lead to balloon migration and occlusion of non-target vessel segments. Endovascular medical devices for blood vessel occlusion include metal coils that are used to fill a portion of the lumen of a blood vessel segment to induce thrombosis and occlusion of the blood vessel segment. There are several major drawbacks to the use of metal coils and basket structures for blood vessel occlusion. First, numerous coils are usually required to occlude the blood vessel segment, resulting in higher costs and longer treatment times. Second, coil placement is difficult to control, often resulting in coil placement in non-target vessel segments. Third, coils only partially fill the blood vessel. The accumulation of thrombus and scar tissue is required to occlude the blood vessel, a process that takes weeks to occur and is sometimes incomplete, often resulting in incomplete occlusion or recanalization and a failed treatment. More recently, endovascular medical devices for blood vessel occlusion have been developed that include basket structures that are used to fill a portion of the lumen of a blood vessel segment to induce thrombosis and occlusion of the blood vessel segment. Although only a single basket structure is usually required to occlude a blood vessel segment, and the devices are generally easier to control, these devices only partially fill the blood vessel and require the accumulation of thrombus and scar tissue to occlude the blood vessel. As with coils, this process that takes weeks to occur and is sometimes incomplete, often resulting in incomplete occlusion or recanalization and a failed treatment.

Therefore, there remains a need for catheter-based medical devices, systems, and methods for the occlusion of blood vessel segments that are simple to perform, result in a rapid, controlled, and complete occlusion, have a low risk of recanalization, device migration, or other complications, and can be purchased at a reasonable cost.

SUMMARY OF THE PRESENT DISCLOSURE

The present invention relates to a medical device for the occlusion, or blockage, of blood vessel segments—including arteries and veins, and other vascular conduits. The medical devices comprise a blockstent, a delivery catheter for delivering and expanding the blockstent, and a component for separating the expanded blockstent and the delivery catheter. The invention further relates to an expanded blockstent left in the lumen of a blood vessel segment. Additionally, the invention includes various forms of blockstents, delivery catheters, and components for separation. Further, the invention includes systems and methods relating to the use of the medical devices, as well as kits comprising medical devices and instructions for use. The invention also includes methods of manufacturing blockstents, delivery catheters, and components for separation.

The walls of blockstents can be formed from a variety of expandable, rigid materials, preferably metals. The metal used to make the wall of a blockstent can be selected from the group consisting of gold, platinum, silver, titanium, vanadium, aluminum, nickel, tantalum, zirconium, chromium, silver, gold, silicon, magnesium, niobium, scandium, platinum, cobalt, palladium, manganese, molybdenum, alloys thereof, and/or combinations thereof. Other metals can be used so long as they are safe to use as an implanted medical device, can be formed into thin walls, and can be expanded from a compressed state and remain expanded in the body, holding their shape under typical conditions. Preferably, the blockstent is made of a ductile metal such as gold, platinum, silver, alloys thereof, and/or combinations thereof. In a fully expanded form, the blockstent can be configured in a variety of sizes and shapes, depending on the size and shape of the blood vessel to be treated, with preferable forms including a cylinder with rounded, hemispherical, or flat ends. Available shapes include, but are not limited to, cylindrical or oblong. Preferably, the blockstent can have an expanded diameter ranging from about 2 mm to about 30 mm. The oblong blockstent can have an expanded length of between about 5 mm to about 60 mm. The blockstent wall has a width, or thickness ranging from about 3 μm to about 180 μm. Such width allows for compression into a small volume and facilitates passage through blood vessels and catheters. For example, blockstents can be folded and compressed to a diameter small enough to pass through 3Fr to 12Fr catheters, such that small, medium, and large diameter blood vessels can be treated, or maneuvered through small vessels, including but not limited to cerebral arteries.

The wall of the blockstent can be uniform or variable, with the thickness changing at different locations on the blockstent. In some blockstent embodiments, the wall of the region near the attachment to the delivery catheter is thicker than the main body of the blockstent, while in other embodiments this region is thinner. In other embodiments, the wall of the blockstent contains an external layer that is porous. This porosity generally can be uniformly distributed, or can be applied only in certain regions, or in a pattern on the surface. In certain embodiments, a blockstent can have a plurality of pores extending through the entire wall.

In other embodiments, the external surface of the wall of the blockstent contains, which in certain instances act to reduce blockstent migration after expansion. These projections may be macroscopic, such as with the hooks or bards seen on other implanted cardiovascular medical devices such as caval filters. For example, a plurality of projections, such as barbs and hooks, can be located on the exterior layer to anchor the blockstent to the surrounding tissue. In a further embodiment, these projections comprise an expansile metal, such as nitinol or fibers. For some embodiments, these projections are microscopic, ranging in length from 0.01 μm to about 157 μm. In other embodiments, these projections are branching.

The surface of the blockstent wall can be configured to increase local thrombus formation and tissue growth into the blockstent wall in order to secure the blockstent in place and reduce the risk of blockstent migration. The wall of the blockstent can further be configured to release solutions that can include drugs, pharmacologically active molecules, or pharmacologic compositions, such as those that would increase the formation of local thrombus, stimulate cell proliferation or the production of extracellular matrix, or increase the rate or extent of tissue growth, such as tissue growth into pores, or around projections, of the wall of the blockstent.

In one embodiment, the blockstent has an exterior layer located on the exterior surface of the wall. The exterior layer may be made from the same materials as the central layer or wall, or can be made of different materials. The exterior layer may be comprised gold, platinum, silver, alloys thereof, or combinations thereof. The exterior layer may also be comprised of polymer, plastic, latex, rubber, an elastomer, fiber material, and combinations thereof. The exterior layer can have a thickness ranging between about 1 μm to about 59 μm.

In one embodiment, the exterior layer has a porous construction. For embodiments with a porous exterior layer, the exterior layer of the blockstent wall can have a plurality of pores ranging in diameter from about 0.01 μm to about 100 μm. The pores allow tissue to grow into the wall of the blockstent. The pores can be uniformly distributed, or can be applied only in certain regions, or in a pattern on the surface. In another embodiment the exterior layer comprises a plurality of projections. These projections can range in length from about 0.01 μm to about 157 μm. In other embodiments, these projections are branching. The projections allow tissue to grow around portions of the wall of the blockstent. The projections can be uniformly distributed, or can be applied only in certain regions, or in a pattern on the surface.

In one embodiment, the porous exterior layer can be configured to release solutions such as drugs, pharmacologically active molecules, pharmacologic compositions, or other compositions that increase the local formation of thrombus rate, or stimulate cell proliferation, extracellular matrix formation, or tissue growth into the pores or around projections of the blockstent wall. Examples of such substances include thrombin, platelet-derived growth factor, Ethiodol®, Sotradecol®, and combinations thereof, and can include both solutions and suspensions. The porous exterior layer can be comprised of any porous material, including metal that can hold fluid or solid material, including drugs, pharmacologically active molecules, or pharmacologic compositions, or any material that promotes thrombosis, cell proliferation, extracellular matrix productions or tissue growth.

Alternatively, the exterior layer can be more smooth, with limited porosity or projections, such as with a polished metal surface. In one embodiment, portions of the exterior layer can be smooth, while other portions can be porous or contain projections. In one embodiment, this surface variation can have a pattern.

In one embodiment, the blockstent has an interior layer located on the interior surface of the central layer or wall. The interior layer may be made from the same materials as the central layer, or can be made of different materials. The interior layer may be comprised gold, platinum, silver, alloys thereof, or combinations thereof. The interior layer may also be comprised of polymer, plastic, latex, rubber, an elastomer, fiber material, and combinations thereof. The interior layer can have a thickness ranging between about 0.1 μm to about 59 μm. Preferably, the interior layer may be an elastomeric coating that strengthens the wall, reduces the leaking of fluid from the blockstent during expansion, or facilitates folding, compression, or expansion of the blockstent.

In another embodiment, the blockstent may include two or more metal regions joined by a flexible polymer and/or elastomer joint. The joint allows for better maneuverability and increased trackability as the blockstent is advanced to the desired location. In other embodiments, the blockstent may include three or more metallic regions that are joined through two or more flexible joints.

The blockstent wall defines an opening that allows for the passage of fluid. An attachment between the blockstent and delivery device is formed whereby the void of the blockstent defined by the inner surface of the wall can be joined in fluid communication with the lumen of a hollow cylindrical member of the delivery device which is configured to allow for the proximal end of the lumen to accept a fluid source and for fluid to pass from the fluid source, through the lumen of the hollow cylindrical member of the delivery device, and into the void of the compressed blockstent, resulting in expansion of the blockstent.

In one embodiment, the fluid used to expand the blockstent is water or a saline solution. In another embodiment, the fluid is a solution of radiopaque contrast material. In another embodiment, solids can be used to expand the blockstent, including solids used in combination with fluids.

In one embodiment, the solids used to expand the blockstent, or to reduce subsequent compression of the expanded blockstent, are selected from the group of metallic or polymeric coils or wires, metallic or polymeric expansile structures, beads, balls, microspheres, radially expansive materials, support structures, or combinations thereof. In another embodiment, the fluid that is used to expand the blockstent can contain drugs or pharmacologically active molecules, such as those that catalyze the formation of thrombus, including thrombin. Fluid, as defined, can be a gas, liquid, or combination thereof.

The blockstent wall defines an opening that allows for the passage of fluid. An attachment between the blockstent and delivery device is formed whereby the two devices are in fluid communication. The opening defined by the wall of the blockstent can have a diameter ranging between about 0.25 mm and about 5 mm. Optionally, the blockstent has a neck integral with the wall, whereby the neck defines an opening that can extend away from the main body of the blockstent, such as with an external neck, or may extend into the void of the blockstent, such as with an internal neck. The neck of the blockstent may be configured to remain open at the end of the procedure, or may be configured to be sealed prior to the end of the procedure.

The present invention also includes a delivery device for positioning and expanding the blockstent. Various configurations of delivery device can be used to advance the blockstent to the desired location and expand the blockstent. Preferably, the delivery device is a delivery catheter. The delivery catheter includes one or more hollow cylindrical members that define one or more lumens. The delivery catheter can be constructed as a single-lumen catheter, wherein the single cylindrical member is dimensioned to deliver the blockstent to a desired location and deliver fluid from a fluid source at the proximal end into the central void of the blockstent at the distal end. When a single cylindrical member with a single lumen is used, generally the medical device is advanced into position through the lumen of a separate guide catheter, which acts to guide the blockstent portion of the medical device to the desired location in the lumen of the blood vessel. Once at the desired location, the blockstent can be expanded and separated from the delivery catheter so that it can remain in the blood vessel while the delivery catheter is removed. For this single lumen embodiment, the catheter does not include a cylindrical member that defines a lumen that is dimensioned to allow for the passage of a guidance member, or guide wire. The wall of the delivery catheter can be comprised of standard catheter materials including a plastic or polymer material such as polyurethane. Further, the wall of the delivery catheter can be additionally comprised of metal reinforcement, such as metal reinforcement that is wound in a coil or braid, or some combination of these materials, as described.

In one embodiment, the delivery device comprises a single lumen delivery catheter wherein the distal end of the delivery catheter is configured to enable a fluid connection between a lumen of the delivery catheter and the central void of the blockstent. When the blockstent is compressed, this delivery catheter can advance the compressed blockstent through a guide catheter and into the lumen of the blood vessel. The delivery catheter also optionally comprises a wire or obturator of a size that fills at least a portion of the lumen of the catheter. The wire or obturator can further comprise a handle to assist removal of the wire or obturator and enable the passage of fluid through the delivery catheter and into the central void of the blockstent to expand the blockstent.

The delivery catheter can also be constructed as a double-lumen catheter, wherein the first cylindrical member is dimensioned to deliver fluid from the fluid source into the central void of the blockstent and a second cylindrical member is dimensioned to pass over the guidance member, which acts to guide the medical device to the desired location in the lumen of the blood vessel. The guidance member is typically a flexible guide wire that may have a soft, flexible tip in a straight, angled, or j-shaped tip configuration.

In a particular embodiment, the delivery catheter includes a hollow cylindrical member that defines a lumen. The cylindrical member has a proximal end that is attached or can be attached to a fluid source. The cylindrical member comprises polyurethane, with a reinforcement of metal in the form of a coil or braid, and a wall thickness between about 0.05 mm and 0.25 mm. The defined lumen has a diameter between about 0.4 mm and 1.0 mm. A wire comprised of nitinol or fibers with a diameter between about 0.3 mm and 0.95 mm is placed in the lumen. A cylindrical blockstent with a wall and flattened ends composed of gold with a wall thickness of 15 $\mu$m, an expanded diameter of 4 mm, and an expanded length of 6 mm is attached to the distal end of the delivery catheter by friction in a manner that allows for the formation of a fluid connection between the lumen of the cylindrical member and the central void of the blockstent. Alternatively, The blockstent can have rounded ends. The blockstent may be folded and compressed into a cylindrical shape at the tip of the delivery catheter.

Various methods can be used to compress the blockstent and enable it to travel through a hollow cylindrical member, or lumen, of a separate guide catheter or through small diameter blood vessels. In one embodiment, the blockstent is folded to form one or more pleats prior to or after attaching the blockstent to the delivery catheter, and the pleats are rolled and compressed, similar to the folding of a non-compliant angioplasty balloon. In another embodiment, the blockstent is flattened into a planar shape, and rolled into a cylindrical shape. In another embodiment, the blockstent is compressed into a compact spherical shape. In another embodiment, the blockstent is folded and compressed into a manner similar to origami. In certain embodiments, the blockstent may be folded and wrapped around the shaft of the delivery catheter.

The blockstent may be attached to the delivery catheter using a variety of materials, components, systems, and methods. The blockstent can be attached to the delivery catheter in a manner wherein the size and shape of the distal end of the delivery catheter and the size and shape of the opening in the blockstent wall are matched so that a friction fit is formed between blockstent and the delivery catheter. In an embodiment of a friction fit, an elastic sleeve or wrap can be placed around the neck of the blockstent and used to further hold the blockstent and the delivery catheter together. In another embodiment of a friction fit, a vacuum can be formed in the catheter to further hold the blockstent and the delivery catheter together. The blockstent can be attached to the delivery catheter using an adhesive, or glue. The blockstent can be attached to the delivery catheter using a weld, or solder. The blockstent can be attached to the delivery catheter by a fitting of mechanical parts on the blockstent and the delivery catheter, such as with a clamp that can be released with a wire, polymer strand, filament, thread, or string that can be loosend or removed.

After expansion of the blockstent in the lumen of a blood vessel segment, the blockstent may be separated from the delivery catheter using a variety of materials, components, devices, systems, and methods. For example, the expanded blockstent may be separated from the delivery catheter using components of the medical device, using a separate and distinct medical device, or combinations thereof. The blockstent may be separated from the delivery catheter using a variety of methods including physical methods, mechanical methods, electrical methods, thermal methods, chemical methods, hydraulic methods, sonic methods, and combinations thereof.

By way of example and not limitation, for electrical methods, the medical device can be configured such that electrolysis can be used to dissolve a metal weld or solder between the blockstent and the delivery catheter, or used to dissolve a portion of the metal blockstent itself. In certain embodiments, an elongated, insulated electrolysis wire or insulated conductor wire can carry an electrical current from the proximal end of the delivery catheter to the distal end of the delivery catheter where it may be electrically coupled to the weld or solder, or to the blockstent itself. A portion of the weld or solder, or a portion of the blockstent itself may lack insulation such that the electrical current traveling through the insulated electrolysis wire or insulated conductor wire will dissolve the portion of the weld, solder, or the portion of the blockstent that lacks insulation, resulting in separation of the blockstent from the delivery catheter. The blockstent can have a neck for example, that can be coated on the inner wall, outer wall, or both, wherein a strip of conductive material left is left exposed, uncoated, or uninsulated and whereby the wire is in electrical contact with the blockstent. During the electrolysis process may separate a portion of the weld material or a portion of the wall of the blockstent into oppositely charged ions. By way of example and not limitation, for mechanical methods, the medical device can be configured such that the delivery catheter is physically separated from the blockstent by cutting or tearing a portion of the blockstent using a flexible loop of wire, polymer strand, filament, string, thread, or snare, or by using one or more blades. A mechanical separation may also occur where the delivery catheter is physically separated from the blockstent by a disengagement of mechanically mated parts, such as a clamp, or by removing a wire, polymer strand, filament, string, or thread that holds the blockstent and the delivery catheter together. By way of example and not limitation, for thermal methods, the medical device can be configured such that an adhesive bond is warmed, causing the adhesive to melt and allowing for separation of the expanded blockstent and the delivery catheter by subsequently pulling them apart. Separation of an expanded blockstent and a delivery catheter may also occur by applying a hydraulic force, by dissolving a bonding medium with a salt, an acid or base, or a chemical, or by applying sound waves such as focused or pulsed ultrasound waves. Another method, involves perforating the neck prior to usage, so that upon expansion the blockstent can be separated from the delivery catheter by pulling them apart at the line of perforation.

By way of example and not limitation, for attachment by friction bonding, the expanded blockstent and the delivery catheter can simply be pulled apart. By way of example and not limitation, for attachment by an adhesive or glue, the blockstent may be separated from the delivery catheter by mechanical mechanism such as by cutting or tearing a portion of the blockstent or the distal portion of the catheter, by electrolysis of a weld, solder, or a portion of the blockstent, or by warming the adhesive bond, causing it to flow. By way of example and not limitation, for attachment by a weld or solder, the blockstent may be separated from the delivery catheter by electrolysis of a weld, solder, or a portion of the blockstent, or by a mechanical mechanism such as by cutting or tearing a portion of the blockstent or the distal portion of the catheter.

The shape and size of the blockstent may be modified after expansion. For example, prior to separation from the delivery catheter, withdrawing fluid from the void of the blockstent can reduce the size of the blockstent. Also prior to separation, a force can be applied to the blockstent through the delivery catheter by advancing the delivery catheter forward or pulling the delivery catheter back, thus modifying the shape of the blockstent. After separation, an external force can be applied to the blockstent by inflating the balloon portion of a balloon catheter adjacent to the blockstent to modify the shape of the blockstent or push a portion of the blockstent towards a blood vessel. In certain embodiments, this can reduce the amount of blockstent that protrudes from the blood vessel into the lumen of the adjacent parent, or native, vessel. Also, the opening of the expanded blockstent can be sealed through a variety of methods, or left open.

The present invention also relates to a method of occluding a segment of blood vessel with a medical device comprising the blockstent and delivery catheter. The method includes the steps of positioning the compressed blockstent in the lumen of the blood vessel segment to be treated using a delivery catheter, expanding the blockstent by passing fluid through the delivery catheter into the void of the blockstent, separating the delivery catheter from the expanded blockstent and, removing the delivery catheter while leaving the blockstent in an expanded state within the blood vessel segment.

One method for placement of an expanded blockstent within a blood vessel segment includes the steps of accessing the vasculature with a needle, inserting a guide wire through the needle, removing the needle, and optionally, inserting a vascular sheath into the blood vessel. The method also includes the steps of advancing a guide catheter over a guide wire until the tip of the guide catheter is within or near the lumen of the blood vessel. The method also includes passing the medical device comprising a compressed blockstent and the delivery catheter through the guide catheter and positioning it in the lumen of the blood vessel. For this method, the delivery catheter portion of the medical device preferably comprises a cylindrical member with a single lumen configured to allow fluid to pass from the proximal end of the delivery catheter to the distal end of the delivery catheter and into the void of the blockstent, and not configured for a guidance member or guide wire. After the compressed blockstent is in position, the blockstent is expanded by passing fluid through the delivery catheter into the central void of the blockstent until the blockstent fills at least a portion of the blood vessel. The delivery catheter is separated from the expanded blockstent and removed, while the blockstent remains in place in an expanded state. The guide catheter and sheath are also removed. Resultantly, the blockstent is expanded so that at least 50% to at least 90% and up to 100% of the luminal surface of the blood vessel is filled by the expanded blockstent, or alternatively that at least 50% to at least 90% and up to 100% of the luminal surface of the blood vessel is in contact with the expanded blockstent. The method may further include the steps of shaping and/or sealing the expanded blockstent. The exterior surface of the blockstent optionally comprises pores or projections. The pores may have a diameter ranging in diameter from about 0.01 µm to about 100 µm. The projections may have a length that ranges between about 0.01 µm to about 157 µm.

Another method for placement of an expanded blockstent within a blood vessel segment includes the steps of accessing the vasculature with a needle, inserting a guide wire through the needle, removing the needle, and optionally, inserting a vascular sheath into the blood vessel. The method also includes the steps of advancing a diagnostic catheter over a guide wire until the tip of the guide wire is within or near the lumen of the blood vessel and removing the diagnostic catheter. The method further includes passing the medical device comprising a compressed blockstent and a delivery catheter over the guide wire, and positioning the compressed blockstent in the lumen of the blood vessel. For this method, the delivery catheter portion of the medical device preferably comprises at least two cylindrical members and two lumens, with one lumen configured to allow fluid to pass from the proximal end of the delivery catheter to the distal end of the delivery catheter and into the void of the blockstent, and another lumen configured for a guidance member or guide wire. After the compressed blockstent is in position, the blockstent is expanded by passing fluid through one of the cylindrical members of the delivery catheter into the blockstent until the blockstent is expanded to fill at least a portion of the blood vessel. Then the delivery catheter is separated from the expanded blockstent and removed, while the blockstent remains in place in an expanded state. Then the guide wire and sheath are also removed. Resultantly, the blockstent is expanded so that at least 50% to at least 90% and up to 100% of the blood vessel is filled by the expanded blockstent, or alternatively that at least 50% to at least 90% and up to 100% of the luminal surface of the blood vessel is in contact with the expanded blockstent. The method may further include the steps of shaping and/or sealing the expanded blockstent. The exterior surface of the blockstent optionally comprises pores or projections. The pores may have a diameter ranging in diameter from about 0.01 μm to about 100 μm. The projections may have a length that ranges between about 0.01 μm to about 157 μm.

The invention includes a kit with a medical device comprising a blockstent and a delivery catheter, and instructions on use. The medical device optionally further comprises components for separation of the expanded blockstent and the delivery catheter. In one embodiment, the instructions include the steps of placing a guide catheter near or within the lumen of the blood vessel, passing the medical device through the guide catheter, and positioning the compressed blockstent in the lumen of the blood vessel. After the compressed blockstent is in position, the instructions further include the steps of expanding the blockstent, until it fills the blood vessel, followed by separating the blockstent from the delivery catheter, and removing the delivery catheter, while the blockstent remains in the blood vessel in an expanded state. The instructions may further include the steps of shaping and/or sealing the expanded blockstent. In another embodiment, the instructions include the steps of placing a guide wire near or within the lumen of the blood vessel, passing the medical device over the guide wire, positioning the compressed blockstent in the lumen of the blood vessel, and removing the guide wire. After the compressed blockstent is in position, the instructions further include the steps of expanding the blockstent until it fills the blood vessel, followed by separating the blockstent from the delivery catheter, and removing the delivery catheter, while the blockstent remains in the blood vessel in an expanded state. The instructions may further include the steps of shaping and/or sealing the blockstent.

In other embodiments, the invention includes a method of manufacturing the blockstent. The method may include forming the wall of the blockstent through electroforming or electroplating on a cylindrical mandrel, a tapered mandrel, or a mold. The method may further include forming exterior or interior layers through electroforming, electroplating, sputtering, vapor deposition, or combinations thereof. The method for forming the external layer may further include methods to form pores or projections. The method further includes the steps of contacting the blockstent with a solution or suspension of a pharmaceutical, drug, or pharmacologically active molecules such that pharmaceutical, drug, or pharmacologically active molecules remain with the blockstent during placement of the blockstent in a blood vessel, thereby delivering the pharmaceutical, drug, or pharmacologically active molecules to a blood vessel segment. With this method, after positioning the expanded blockstent in the lumen of the blood vessel and leaving it in place, at least some of the molecules leave the blockstent and diffuse into the surrounding cells, tissues spaces, or fluids.

As such, a medical device comprising a blockstent and a delivery catheter is provided that can be used to occlude a segment of a blood vessel.

DESCRIPTION OF FIGURES

FIGS. 1A-B are perspective views of embodiments of the blockstent of the medical device.

FIG. 2 is a plan view of an embodiment of the delivery catheter of the medical device.

FIGS. 3A-B are plan views of an embodiment of the medical device.

FIGS. 5A-B are perspective views of embodiments of the blockstent of the medical device.

FIG. 6 is a plan view of a longitudinal view of an embodiment of the delivery catheter of the medical device.

FIGS. 7A-B are plan views of an embodiment of the medical device.

FIG. 10 is a perspective view of an embodiment of the blockstent after placement of an internal support structure.

FIG. 11 is a perspective view of an embodiment of the blockstent wherein the shape of the blockstent is being changed by applying an external force using a balloon.

FIGS. 12A-B are plan views of embodiments of the blockstent with external surface projections for anchoring means the blockstent to the surrounding tissues.

FIGS. 16A-B are cross-sectional views along a longitudinal axis of embodiments of the delivery catheter of the medical device.

FIGS. 17A-B is a plan view of an embodiment of the medical device with a lumen configured to accept a guide catheter, rather than a guide wire.

FIGS. 23A-B are a perspective and an axial and cross-sectional view, respectively, of embodiments of the delivery catheter of the medical device wherein the delivery catheter has been advanced through the lumen of a guide catheter.

FIG. 24 is a perspective view of a partial cross-section of an embodiment of the medical device wherein the neck of the blockstent is attached to the delivery catheter, with an elastomeric sleeve holding the neck of the blockstent to the delivery catheter, and wherein the blockstent is expanded.

FIGS. 25A-B are a perspective view and plan view, respectively, of an embodiment of the medical device wherein the blockstent is attached to the delivery catheter with and adhesive that can be warmed with a resistive heating element.

FIG. 26 depicts a blood vessel filled by two blockstents.

FIG. 27 is a perspective view of a means for inflating or deflating a blockstent.

DETAILED DESCRIPTION

Figure 4A:
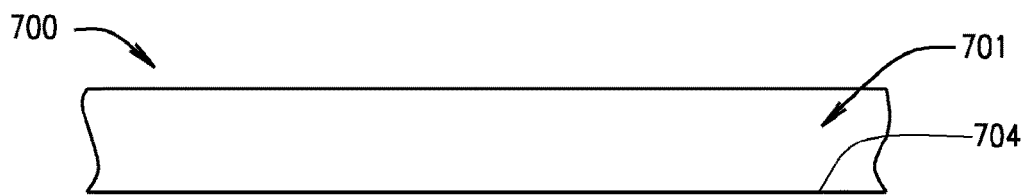
FIGS. 4A-E are plans views of an embodiment of the medical device in a sequence of positioning, expanding of the blockstent, followed by separation of the blockstent from the delivery catheter, wherein the medical device does not have a cylindrical member with a lumen configured for a guidewire.
Figure 4B:
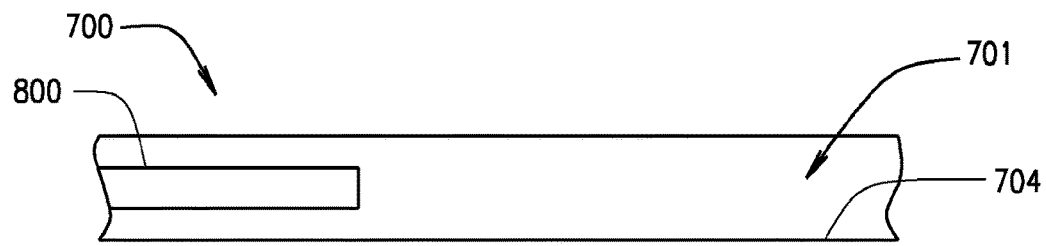
Figure 4C:
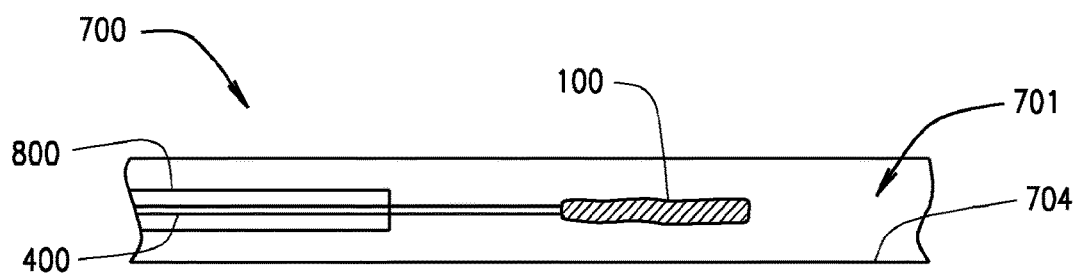

The present invention relates to a medical device comprising an expandable metal structure known as a "blockstent" and a delivery catheter. The blockstent is a thin-walled stent-like, cylindrical, device that can be expanded into a semi-rigid form that can remain in the body for an extended period. Specifically, the blockstent is configured for use in occluding segments of arteries, veins, and other biological conduits. The delivery catheter is configured to deliver the blockstent to a blood vessel and to provide a pathway, through a cylindrical member or lumen, for fluid to move into the central void of the blockstent, in order to expand it and fill at least a portion of the lumen of the blood vessel.

A cylindrical embodiment of the blockstent 100 with flat ends is shown in FIG. 1A in an expanded state. This embodiment has an external proximal neck 116 that defines an opening 112 for the passage of fluids, liquids, gases, or solids into the central void of the blockstent. Another cylindrical embodiment of the blockstent 100 is shown in FIG. 1B in an expanded state. This embodiment has an internal neck 116 that defines an opening 112, also for the passage of fluids, liquids, gases, or solids into the central void of the blockstent. Embodiments of the delivery catheter 400 are shown in FIG. 2 and in FIGS. 3A-B.

An embodiment of the medical device 500 is shown in FIGS. 3A-B. In FIG. 3A the blockstent 100 is in a compressed state, which optionally includes pleats or folds. In FIG. 3B the blockstent 100 is in an expanded state. Expanding the blockstent 100, as used herein, can refer to partial or complete expansion of the blockstent 100 using a fluid, a liquid, a gas, a solid, or a combination thereof. The delivery catheter 400 is used to advance the blockstent 100 into the lumen of the blood vessel. The delivery catheter 400 is also used to deliver a fluid, liquid, a gas, a solid, or a combination thereof, to expand the blockstent 100 in the lumen of the blood vessel. In one embodiment, an electrolysis wire 320 or an insulated conductor wire is connected to either a weld, or solder joining the blockstent and the delivery catheter, or to the blockstent itself.

Figure 4D:
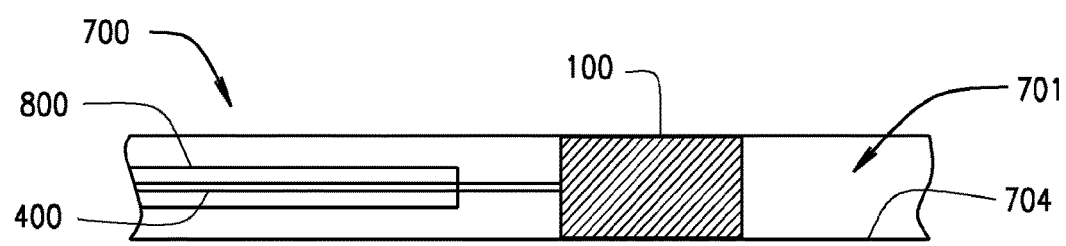
Figure 4E:
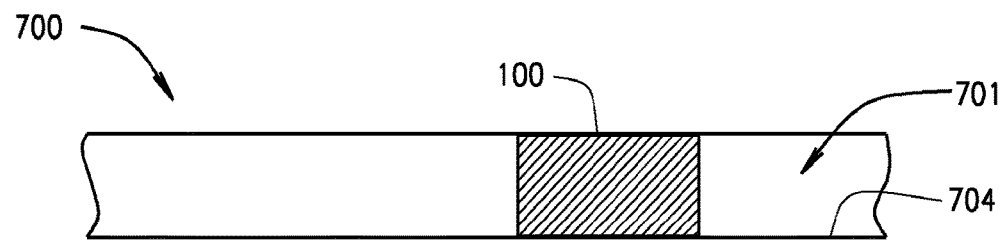

As shown in FIGS. 4A-E, in one embodiment of the medical device 500, the delivery catheter 400 advances the attached compressed blockstent 100 through the lumen of a larger guide catheter 800, beyond the distal end of the guide catheter, and into the lumen 701 of the blood vessel 700. Once the compressed blockstent 100 has been placed in the lumen 701 of the blood vessel 700, the removable wire or obturator 404 is removed from the delivery catheter. The removable wire or obturator 404 may include a handle 408 or other device to facilitate insertion and removal. Then, a fluid source, such as the syringe 314 can be connected to the connection port 406 and fluid can be moved from the syringe 314 into the central void or space 108 of the blockstent 100, resulting in expansion of the blockstent within the lumen 701 of the blood vessel 700 and filling of the blood vessel. As shown in FIGS. 4D-E, after the blockstent 100 is expanded, the delivery catheter 400 and the blockstent 100 are separated and the delivery catheter and guide catheter 800 are removed while leaving the expanded blockstent in the lumen 701 of the blood vessel 700. A variety of methods and devices can be used to separate the catheter from the blockstent 100. In one embodiment, the delivery catheter 400 comprises an electrolysis wire 320 or an insulated conductor wire. For this embodiment, after the blockstent 100 is expanded, a DC current is applied to the electrolysis wire 320 or the insulated conductor wire to dissolve a portion of the weld or solder 316 between the blockstent 100 and the delivery catheter 400 or alternatively to dissolve a portion of the blockstent 100. Once the weld or solder 316 is dissolved, or alternatively a portion of the blockstent 100 is dissolved, the delivery catheter 400 is separated from the blockstent and the delivery catheter and the guide catheter 800 are removed.

Another cylindrical embodiment of the blockstent 100 is shown in FIG. 5A in an expanded state. This embodiment has an external proximal neck 116 that defines an opening 112 for the passage of fluids, liquids, gases, or solids into the central void of the blockstent. This embodiment also has an external distal neck 118 that defines an opening 114 for the passage of a guide wire 302. Another embodiment of the blockstent 100 is shown in FIG. 5B in an expanded state. This embodiment has an internal proximal neck 116 that defines an opening 112, also for the passage of fluids, liquids, gases, or solids into the central void of the blockstent. Further, this embodiment has an internal distal neck 118 that defines an opening 114 for the passage of a guide wire 302.

Another cylindrical embodiment of the medical device 500 is shown in FIGS. 7A-B. In FIG. 7A the blockstent 100 is in compressed state, which optionally includes pleats or folds. In FIG. 7B the blockstent 100 is in an expanded state. The delivery catheter 300 is used to advance the blockstent 100 over a guide wire 302 and into the lumen of the blood vessel. The delivery catheter 300 is also used to deliver a fluid, liquid, gas, solid, or a combination thereof, to expand the blockstent 100 in the lumen 701 of the blood vessel 700. In one embodiment, an insulated conductor wire or an electrolysis wire 320 is connected to either a weld, or solder joining the blockstent and the delivery catheter, or to the blockstent itself.

Figure 8A:
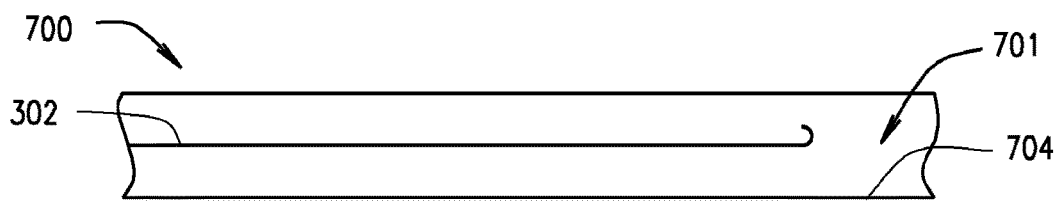
FIGS. 8A-E are plans views of an embodiment of the medical device in a sequence of positioning, expanding of the blockstent, followed by separation of the blockstent from the delivery catheter, wherein the medical device has a cylindrical member with a lumen configured for a guidewire.
Figure 8B:
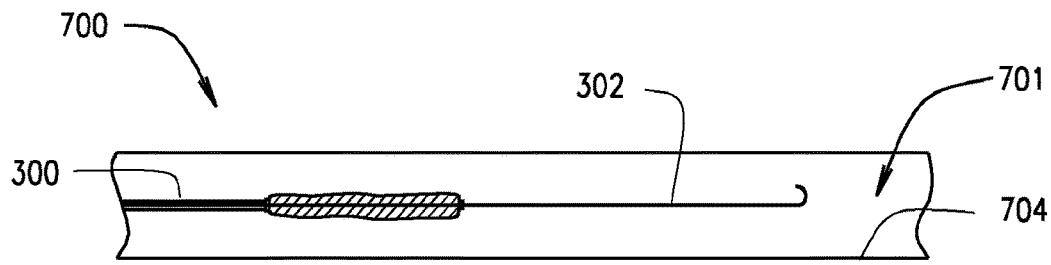
Figure 8C:
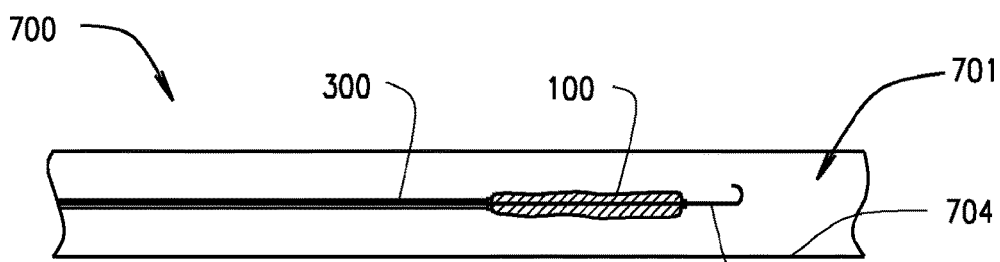
Figure 8D:
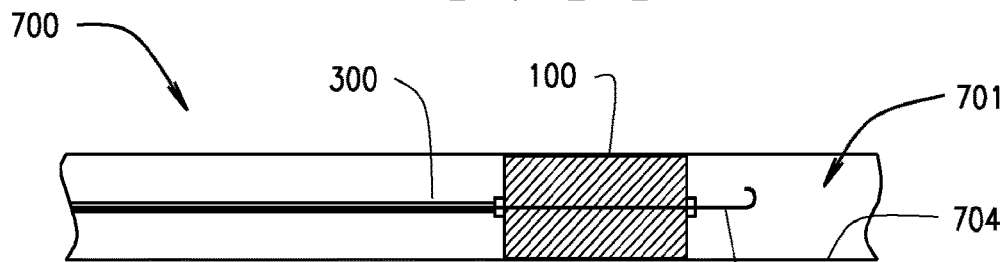
Figure 8E:
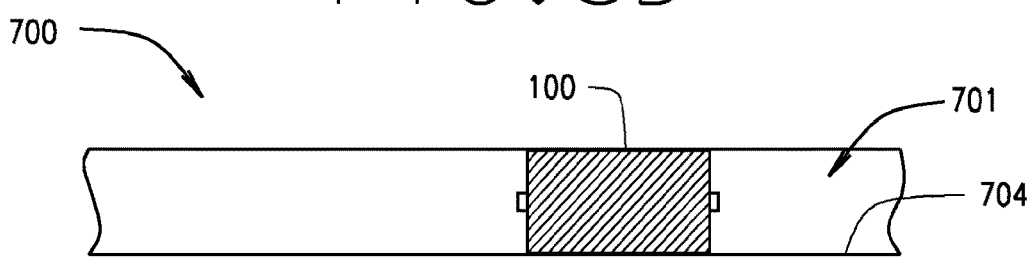

As shown in FIGS. 8A-E, in one embodiment of the medical device 500, the delivery catheter 300 advances the attached compressed blockstent 100 over a guide wire 302 and into the lumen 701 of the blood vessel 700. Once the compressed blockstent 100 has been placed in the lumen 701 of the blood vessel 700, the guide wire 302 is removed. Then the wire or obturator 404 is removed from the delivery catheter 300. The wire or obturator 404 may include a handle 408 or other device to facilitate insertion and removal. Then, a fluid source, such as the syringe 314 is connected to the connection port 308 and fluid is moved from the syringe 314 into the central void or space 108 of the blockstent 100 resulting in expansion of the blockstent until it fills at least a portion of the lumen of the blood vessel 701. As shown in FIG. 8D-E, after the blockstent 100 is expanded, the delivery catheter 300 and the blockstent 100 are separated and the delivery catheter is removed while leaving the expanded blockstent 100 within the lumen 701 of the blood vessel 700. In one embodiment, the delivery catheter comprises an electrolysis wire or an insulated conductor wire is connected or electrically coupled to either a weld or solder joining the blockstent and the delivery catheter, or to the blockstent itself. For this embodiment, after the blockstent 100 is expanded, a DC current is applied to the electrolysis wire 320 or insulated conductor wire to dissolve a portion of the weld or solder 316 between the blockstent 100 and the delivery catheter 300 or alternatively to dissolve a portion of the blockstent 100. Once the weld or solder 316 is dissolved, or alternatively a portion of the blockstent 100 is dissolved, the delivery catheter 300 is separated from the blockstent 100 and the delivery catheter 100 and the guide catheter 800 are removed.

The medical device 500 can be used as part of various methods and medical kits to occlude a blood vessel or other biological conduit, such as a ductus arteriosus, bronchus, pancreatic duct, bile duct, ureter, and fallopian tube. Alternatively, these systems, methods and medical kits can be used to treat a variety of medical conditions by using the systems, methods, and medical kits can be used to occlude biological conduits in patients in need thereof, the biological conduits including arteries, veins, vascular structures, ducts, airways, bile ducts, pancreatic ducts, enterocutaneous fistulas, ureters, fallopian tubes and urethras, among others. The medical kit includes the medical device and instructions for use. The medical kit may also contain additional components for carrying out a variety of treatments using the medical device 500.

A typical method for using the medical device 500 to occlude a blood vessel includes accessing the vascular system of a human with a needle, passing a guidance member, or guide wire, 302 into the vessel, optionally placing a vascular sheath, advancing the medical device comprising a compressed blockstent 100 and a delivery catheter 300 or 400 and advancing it until the compressed blockstent is located in the lumen 701 of a blood vessel 700. Then the blockstent 100 is expanded by passing a fluid, liquid, gas, or solid material, or combinations thereof, through the delivery catheter and into the central or internal void or space 108 of the blockstent. The delivery catheter and the expanded blockstent are then separated and the delivery catheter is removed from the body, while the expanded blockstent remains in place within the lumen 701 of the blood vessel 700. The position of the blockstent 100 during and after the procedure may be monitored by any suitable methods, including fluoroscopy, computed tomography, MRI and ultrasound, including intravascular ultrasound.

The Blockstent

Figure 9A:
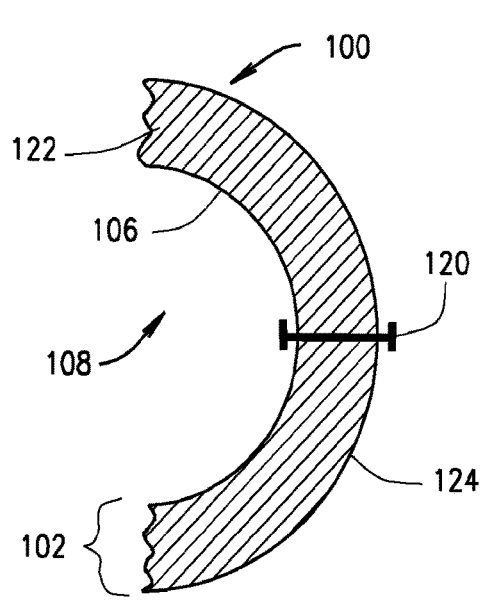
FIGS. 9A-D are hemispherical cross-sectional views taken along a diameter of embodiments of the blockstent.
Figure 9B:
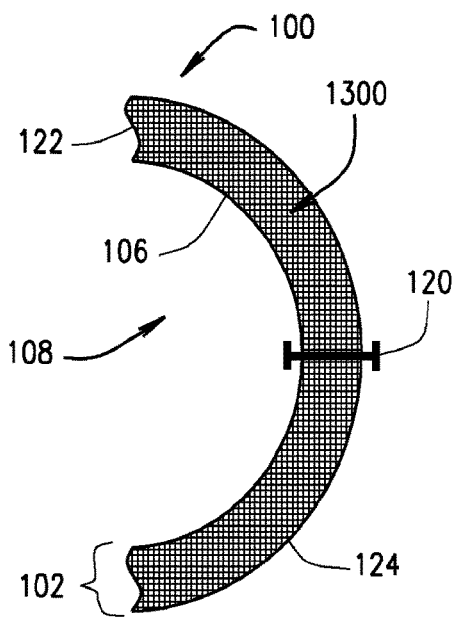

The blockstent 100 may be composed of a single continuous layer or wall 102, as shown in FIG. 9A. The blockstent wall 100 comprises a material, preferably a metal that is biocompatible and ductile, that can form a thin-wall construction, and can assume a variety of shapes after expansion. By way of example and not limitation, the metal can be selected from the group consisting of gold, platinum, silver, nickel, titanium, vanadium, aluminum, tantalum, zirconium, chromium, silver, magnesium, niobium, scandium, cobalt, palladium, manganese, molybdenum, alloys thereof, and combinations thereof. Preferred metals include gold, platinum, and silver, alloys thereof, and combinations thereof. Alternative materials to metal can be used, such as a polymer, plastic, latex, rubber, an elastomer, fiber material, and combinations thereof. Blockstents can be made from alternative materials that can be formed into thin-walled structures that are sufficiently rigid or semi-rigid to tolerate compression and expansion, and can maintain an expanded state in vivo. Alternative materials include polymers or plastics that are reinforced with metal coils or braids, and other materials with similar properties. The materials comprising the wall of the blockstent and the thickness of the wall of the blockstent are selected such that the blockstent 100 has sufficient rigidity to remain in an expanded state in vivo under typical physiologic conditions after expansion and separation from the delivery catheter, even where the pressure inside and outside the central void or space 108 of the blockstent is the same or similar. The central layer 122 of the blockstent wall 102 has an interior surface 106 and exterior surface 124 that define a wall thickness 120. In particular, for FIGS. 9A and 9B, the distance between the interior surface 106 and the exterior surface 124 is the overall wall thickness 120 of the wall 102. Preferably, the central layer 122 of the blockstent wall 102 has a thickness 120 from about 3 μm to about 180 μm. The wall thickness 120 can be uniform. For example, the blockstent wall 102 may have a uniform thickness of 3 μm, 5 μm, 10 μm, 15 μm, 20 μm, 30 μm, 40 μm, 50 μm, 60 μm, 120 μm, or 180 μm. Alternatively, the thickness of the blockstent wall at different locations may vary in thickness. Alternatively, the blockstent 100 may be composed of a single porous layer or wall 122, as shown in FIG. 9B, with pores 1300 wherein at least some pores extend all the way from the internal surface 106 to the external surface 124. For this embodiment, the wall 102 may be of a uniform thickness or a varied thickness.

Figure 9C:
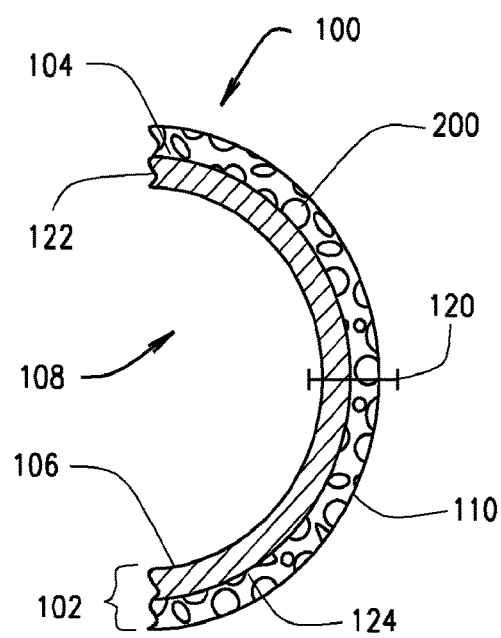
Figure 9D:
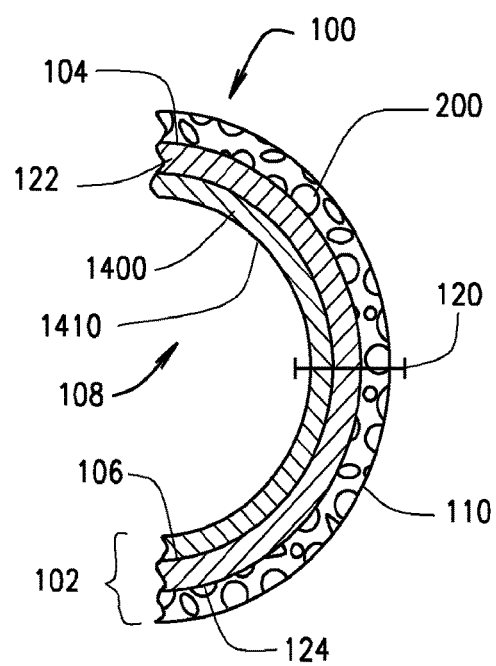

Alternatively, the blockstent 100 may have an additional coating or layer on the exterior surface 124 of the central layer 122, as shown in FIG. 9C. The blockstent wall 102 and any additional exterior layers define an exterior surface 110 that, when expanded, contacts the internal wall of the blood vessel. The exterior layer 104 can be of a uniform or varied thickness, preferably between about 1 μm and about 59 μm. The exterior coating or layer 104 may be porous and contain a plurality of pores 200, as shown in FIGS. 9C and 9D. Alternatively, the exterior layer 104 can be smooth, with limited porosity or projections. For example, the exterior layer 104 may be a polished metal surface. In one embodiment, portions of the exterior layer 104 can be smooth, while other portions can be porous or contain projections. In one embodiment, the surface variations can include a pattern. In particular for FIG. 9C, the distance between the interior surface 106 and the exterior surface 110 is the overall wall thickness 120 of the wall 102.

The porous or spongy nature of the exterior layer 104 can contain (or be configured to contain) solutions that include drugs, pharmacologically active molecules, or pharmaceutical compositions within the pores 200. As such, solutions such as drugs, pharmacologically active molecules, or pharmaceutical compositions can be delivered to the treatment site. Drugs, pharmacologically active molecules, or pharmaceutical compositions that promote thrombosis, stimulate cell proliferation or extracellular matrix productions, or tissue growth are examples that can be placed in the pores 200. The drugs, pharmacologically active molecules, or pharmaceutical compositions are incorporated into the pores 200 of the wall or the exterior layer 104 prior to positioning the blockstent 100 at the desired location. The drug compositions may be delivered into the pores 200 via capillary or wicking action. The pores 200 range from about 0.01 µm to about 100 µm in diameter. Pore diameters for each blockstent may vary according to the specific drugs, pharmacologically active molecules, or pharmaceutical compositions to be incorporated and the desired rate of release from the blockstent in vivo. By way of example and not limitation, the blockstent 100 may have a porous exterior layer 104 where the pore diameter averages from about 0.01 µm to about 0.05 µm, about 0.05 µm to about 0.5 µm, 0.5 µm to about 5 µm, about 5 µm to about 25 µm, about 25 µm to about 100 µm, about 0.05 µm to about 100 µm or about 0.01 µm to about 100 µm for the blockstent.

The pharmaceutical drugs, pharmacologically active molecules, or pharmaceutical compositions may include thrombin, platelet-derived growth factor, Ethiodol®, Sotradecol®, or combinations thereof. Other pharmaceutical compounds and compositions that promote thrombosis and coagulation or stimulate cell proliferation, the synthesis of extracellular matrix, or the growth of tissue into the porous external wall of the blockstent 100 may also be used. Such drugs or pharmacologically active molecules pharmaceutical compositions may include molecules to promote cell proliferation, extracellular matrix production, or tissue growth, such that the expanded blockstent 100 will become more firmly attached to the tissue at the treatment location. The dosages and manner in which the pharmacologically active molecules, or pharmaceutical compositions are incorporated into the blockstent wall or exterior layer 104 are a matter of choice depending on the treatment performed. Other compounds may be used to promote blood clotting or thrombosis around the blockstent. For embodiments of the blockstent 100 with a porous layer 104, over time, the blockstent 100 remains expanded with the blockstent eventually becoming affixed to the surrounding tissue. The exterior surface of the ballstent may also comprise one or more projections, as described, that can increase the strength of the attachment of the expanded blockstent to the adjacent tissue, and thereby reduce the risk of blockstent movement or migration. The projections may have a length that ranges between about 0.01 µm to about 157 µm. The projections can be microscopic and can have a branched construction. In some embodiments, the projections are rigid, or semi-rigid. In other words, embodiments, the projections are flexible and hair-like, and may further comprise globular ends, similar to the projections on the surface of the footpad of the gacko.

Alternatively, the blockstent 100 may comprise an additional layer or liner 1400 on the interior surface 106 of the wall 102 or central layer 122, as shown in FIG. 9D. The interior layer may be made from the same materials as the central layer, or can be made of different materials. The interior layer may be comprised gold, platinum, silver, alloys thereof, or combinations thereof. The additional layer 1400 on the interior surface of the wall 106 of the central layer 122 of the blockstent 100 may also be composed of a polymer, plastic, latex, rubber, woven or knitted fiber material, metal, or another material, or combinations thereof. Preferably, the interior layer 1400 is an elastomeric coating that is bonded to the interior surface 106 of the central layer 122. The interior layer 1400 can be a variety of thicknesses, preferably ranging between about 0.1 µm and about 59 µm. The total thickness of the wall 102, including the central layer 122, the exterior layer 104, and the interior layer 1400 is preferably between 2 µm and 60 µm, regardless if the wall contains one, two, three, or more layers. The interior layer 1400 can be comprised of polymers, latex, or elastomers. In a preferred embodiment, the interior layer 1400 is comprised of Parylene™. The interior layer 1400 adds mechanical properties (such as strength) to the wall 102. Further, the interior layer 1400, optionally, can form a seal that prevents the escape of fluids from the blockstent 100, should the central layer 122 of the wall 102 contain a defect, such as a defect or hole. The blockstent central layer 122 and any additional layers define an interior surface 106 or 1410, such that when the blockstent is expanded, with a fluid, liquid, gas, or solid, a central void or space 108 is defined. In particular for FIG. 9D, the distance between the interior surface 1410 and the exterior surface 110 is the overall wall thickness 120 of the wall 102.

Advantageously, the blockstent 100 can be delivered into the lumen 701 of a blood vessel segment 700, expanded, and then separated from the delivery catheter 300, such that the delivery catheter can be removed while the blockstent remains in place filling a portion, substantially all, or all of the lumen of the blood vessel in an expanded state. The expanded blockstent 100 will typically conform to the shape of the blood vessel segment cavity in which it is placed. The expanded blockstent 100 can also be shaped with external force, such as a physical force applied by the inflated balloon portion 1102 of an adjacent balloon catheter 1100, as shown in FIG. 11. With precise placement and shaping, the blockstent can be positioned such that the treated blood vessel segment is completely or substantially filled and occluded without any portion of the blockstent sealed, and further with none of the blockstent, or a minimal amount of the blockstent, extending into the lumen of an adjacent blood vessel segment that is not intended for treatment the parent vessel 1202, from which the aneurysm has formed.

As illustrated in FIGS. 1A-B and FIGS. 3A-B, the blockstent 100 has one or more openings 112 and 114 defined by the wall 102 or by one or more necks 116 and 118. Fluid can enter the opening 112 to expand and move into the central void or space 108 defined by the interior surface 106 or 1410, thereby expanding the blockstent. In various embodiments, one or both of the necks 116 and 118 can project away from the wall 102 of the blockstent 100 or they can project into the central void or space 108 of the blockstent 100. The necks 116 and 118 can be used for attaching the blockstent to the delivery catheter and may function in separating the blockstent 100 from the delivery catheter. Additionally, the necks 116 and 118 can be designed and dimensioned such that the opening 112 can be closed or partially closed before, during, or after separation of the expanded blockstent from the delivery catheter. One or more openings 112 or 114 may remain open. Optionally, before, during, or after separation, the necks 116 and 118 may be folded, pinched or closed to form a seal. The necks 116 and 118 have a length ranging between about 0.5 mm and 60 mm, preferably a length between about 0.5 mm and about 5 mm. The necks 116 and 118 may define the openings 112 and 114, respectively, having diameters between about 0.25 mm and about 2 mm. The necks 116 and 118 may protrude into the central void or space 108 for a length ranging between about 1 mm and 60 mm, and preferably for a length between about 0.5 mm and 5 mm, while defining the openings 112 and 114, respectively, having diameters between about 0.25 mm and about 5 mm, and preferably having diameters between about 0.25 mm and about 5 mm. The thickness of the wall of either or both of the necks 116 and 118 may be the same as the main body of the blockstent or may be thinner than the wall of main body of the blockstent. Similarly, the thickness of the wall of either or both of the necks 116 and 118 may be thicker than the wall of the main body of the blockstent. Preferably, either or both of the necks 116 and 118 have a wall thickness between about 3 µm and about 60 µm. With an embodiment of the blockstent wherein the neck(s) extends into the central void or space 108 of the blockstent 100 the external surface of the blockstent retains a more rounded surface contour, and therefore there may be a reduced risk of damage to the blood vessel wall or the adjacent tissue with placement of the blockstent. One or both of the necks 116 or 118 can be coated with insulation on the inner wall, outer wall, or both, wherein a strip of conductive material, including an uncoated or uninsulated section of a weld or solder, or portion of the blockstent itself, is left exposed, uncoated, or uninsulated and whereby a conductive wire is in electrical contact with the blockstent 100 uncoated or uninsulated portion of the weld or solder, or blockstent 100.

Various expanded blockstent shapes are acceptable, as required to treat blood vessel segment of various shapes, including circular, oblong, and irregular. Regardless of the formed shape, when a blockstent is expanded in the lumen or cavity 701 of a blood vessel 700, the blockstent is designed to conform, at least partially, to the shape of the cavity.

In various embodiments, the dimensions of the blockstents 100 are selected based upon the size and shape of the blood vessel segment being treated. Preferred shapes of the blockstent 100 include cylindrical, oblong, and irregular. For example, the blockstent 100 may a cylinder with rounded, hemispherical, or flat ends. The diameter of the cylindrical expanded blockstent 100 ranges from about 2 mm to about 30 mm, and preferably has an expanded diameter ranging from about 1 mm to about 20 mm. The expanded length of oblong blockstents preferably ranges between about 5 mm to about 60 mm. The blockstent 100 may have an expanded volume that ranges between about 0.005 cc to about 65 cc. In preferred embodiments, the expanded diameter of the cylindrical blockstent 100 ranges from about 2 mm to about 10 mm, while the preferred expanded volume ranges from about 0.004 cc to about 40 cc. In preferred embodiments, the expanded length of the oblong blockstent 100 ranges between about 2 mm to about 20 mm.

In other embodiments, one or more portions of the blockstent wall 102 may be thicker than the remaining portions of the wall. By way of example and not limitation, the wall in the central portion middle of the body of the blockstent may be thicker than the wall in the proximal and distal portions of the blockstent, or in the neck(s) the wall of a neck may be thicker or thinner than the main body of the blockstent. Optionally, the entire blockstent wall can be porous, as shown in FIG. 9B, with pores extending from the internal surface 106 to the external surface 124. During expansion of the blockstent of this embodiment, fluid may travel under pressure from the central void or space 108 of the blockstent, through the wall 102 and leave the blockstent at the exterior surface 124. Preferably, for this embodiment, the pores range from 10 µm-1000 µm in diameter.

The blockstent comprises a central wall or layer 122, optionally with an exterior wall or layer 104, and also optionally with an interior wall or layer 1400, as shown in FIG. 9C. As mentioned, the construct of the central layer or wall 122 and the layers 104 and 1400 can be uniform, porous, or combinations thereof.

In one construction, the central layer or wall 122 of the blockstent 100 is continuous and comprised of gold. To this preferred construction, an exterior layer 104 comprised of porous gold can be added. Additionally, an interior layer 1400 comprised of Parylene™ may be present. In certain embodiments wherein electrolysis is used to separate the expanded blockstent 100 from the delivery catheter, certain portions of the blockstent (such as the neck, or body) are coated with an insulator polymer, such as Parylene™ (including the external surface, the internal surface, or both the internal and external surfaces) while a portion of the neck or body remains uncoated or uninsulated. In this instance, the uncoated or uninsulated portion is solubilized by the passage of an electrical current into the uncoated or uninsulated portion during electrolysis. In certain embodiments, the uncoated or uninsulated portions are created by masking during the coating process. In other embodiments, the coating or insulation is removed from the uncoated portions, as through etching or ablation, such as with laser etching or laser ablation.

The central void or space 108 of the blockstent 100 can be filled with fluids, solids, or combinations thereof. A fluid is a substance having particles that easily move and change their relative position without a separation of the mass. Fluids that can be used to inflate or expand the blockstent 100 include liquids, gases, and combinations thereof. By way of example and not limitation, the fluid may be water, a saline solution, a radiographic contrast solution, or a mixture thereof. In one embodiment, the fluid may further include a solution or suspension of a drug or pharmacologically active molecules or a pharmaceutical preparation. By way of example and not limitation, the drug, pharmacologically active molecules, or pharmaceutical preparation may increase local thrombosis, cell proliferation, extracellular matrix production, or tissue growth into of around the wall 102 of the expanded blockstent when it is positioned in the lumen of a blood vessel segment.

In one embodiment, the shape of an expanded blockstent is maintained by placing solid material or support structures into the central void or space 108 of the expanded blockstent 100. Examples of this solid material include metal or polymeric coils or wires, metal or polymeric solid support structures, radially expansile materials, beads, particles, spheres, or microspheres. In certain embodiments, these solid materials can also be used to help expand the blockstent. In other embodiments, these solid materials are added after the blockstent expansion. In one embodiment, as shown in FIG. 10, the blood vessel 700 adjacent to the blood vessel 1202 is filled with a blockstent containing at least one coil or expansile wire 1204. In one aspect, the blockstent 100 may be expanded by the coil or expansile wire 1204 only, while in other aspects, the blockstent 100 may be expanded by a fluid and the solid materials may be added later to provide support to maintain the expanded shape of the blockstent. Other suitable biocompatible solid materials may also be used. The solid fill members can function as a lattice to insure the structural integrity of the blockstent 100. For example, the coil 1204 can promote the structural integrity of the blockstent 100 and reduce compression of the blockstent. In one embodiment, solid material may be designed and manufactured to match a ballstent of a particular size or shape, and may be packaged as part of the medical device for use with the packaged ballstent.

Embodiments of the blockstent can include features designed to secure the blockstent in place once it has been expanded in the lumen of a blood vessel. These features can be biological or physical, or a combination thereof. In one embodiment, the exterior surface 110 of the blockstent 100 may be coated with molecules that can bind to adjacent thrombus or tissue. These molecules can be affixed to the blockstent through a variety of methods, including chemical bonds such as with hydrogen bonding or covalent bonding. Alternatively, these molecules can be affixed to the blockstent through encapsulation of a porous layer or encapsulation of projections. Representative molecules that can be affixed to the wall of blockstents include fibrin, and molecules that can link to fibrin through covalent and non-covalent bonding. With such a coating, the blockstent can be anchored to the fibrin-rich clot that forms between the blood vessel and the blockstent. In another embodiment, the blockstent 100 may comprise a porous external layer or wall 104 or a wall with external projections to promote thrombus formation on the external surface 110 or in the pores 200 of the blockstent and promote cell proliferation, extracellular matrix production, or tissue growth into or around the wall 102 of the ballstent 100 the porous layer, such that the blockstent 100 will, over time, become more strongly attached to the tissue in the adjacent blood vessel wall. As shown in another embodiment, the wall 102 or exterior surface 124 or 110 of the ballstent 100 further comprises one or more projections therefrom, which can be used to anchor the blockstent 100 to the surrounding tissue walls specifically of the blood vessel and hold the blockstent in the desired location. In a macroscopic form, the projections may be composed of nitinol or fibers or any other suitable biocompatible material. The projections may be straight, curved, hook-shaped, or configured as pigtail hooks 1800 as shown in FIG. 12A. FIG. 12B depicts an expanded blockstent 100 that is anchored to the wall 1802 of a blood vessel 1804. The size and shape of the projections may be selected based upon the condition being treated, and may be designed and dimensioned to provide sufficient anchoring support without causing excessive damage to the wall of the blood vessel or the surrounding tissue. Alternatively, microscopic projections or filaments may be used to anchor the blockstent. For some embodiments, these microscopic projections range in length from 0.01 μM to about 157 μm, and can be straight or branching.

Figure 13:
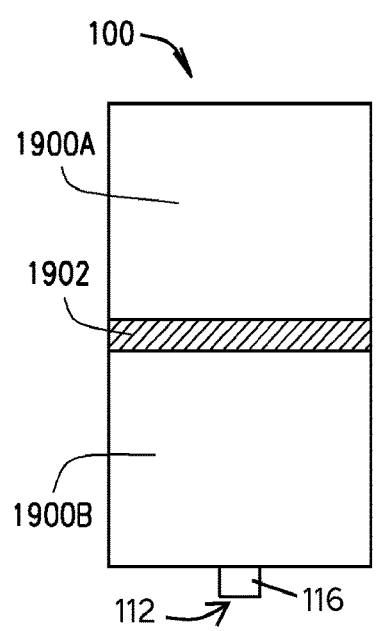
FIG. 13 is a plan view of an embodiment of the blockstent having an elastomer joint.

In order to facilitate advancement of the blockstent through the vascular system, some embodiments of the blockstent 100 comprise two or more metallic portions 1900A-B that are joined by a flexible joint 1902, as shown in FIG. 13. In certain embodiments, this flexible joint can comprise a variety of materials that are flexible and biocompatible, including various polymers or elastomers. The joint 1902 allows for better maneuverability and increased trackability as the compressed blockstent is advanced to the desired location. In other embodiments, the blockstent 100 may include three or more metallic or rigid portions that are joined through two or more flexible joints.

In order to facilitate advancement of the blockstent through the vascular system, the blockstent 100 can be compressed into various shapes and dimensions. Optionally, this compression can include various forms and patterns of folding or pleating. For example, one or more pleats can be made in the blockstent 100 and then the pleats can be wrapped into a cylindrical shape. Alternatively, the blockstent 100 may be flattened into a planar shape and then rolled into a cylindrical shape. Alternatively, the blockstent 100 may be compressed into a compact spherical shape. Additionally, the portions of the blockstent 100 may be twisted or braided during compression. In certain instances, the blockstent may be compressed around the delivery catheter 300, as in FIG. 7A. In other instances, the blockstent may be compressed around the obturator 404, as in FIG. 3A. In other embodiments, the blockstent 100 may be compressed on itself, without a central catheter or obturator.

Figure 14A:
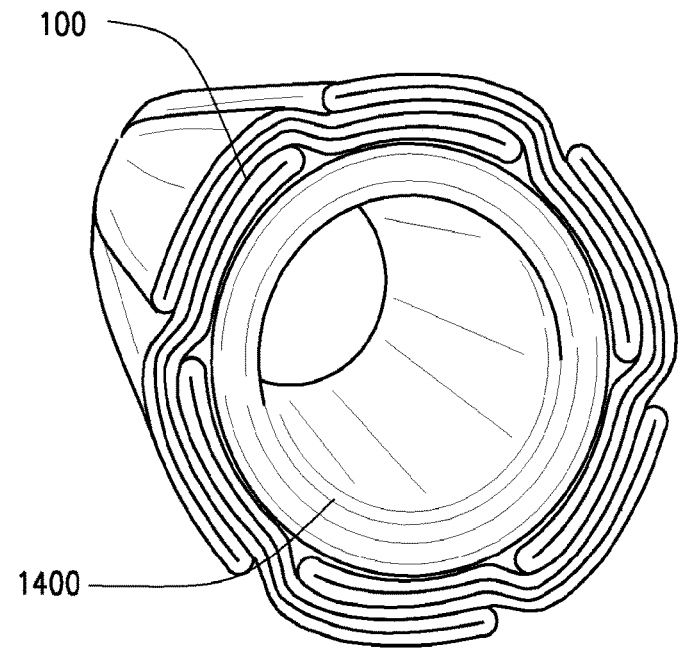
FIG. 14A is a perspective view of an embodiment of a blockstent as compressed against a delivery catheter.
Figure 14B:
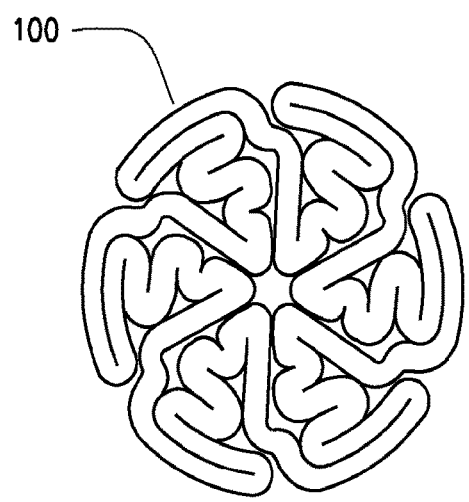
FIG. 14B is a perspective view of an embodiment of a compressed blockstent.
Figures 15A, 15B, 15C, 15D:
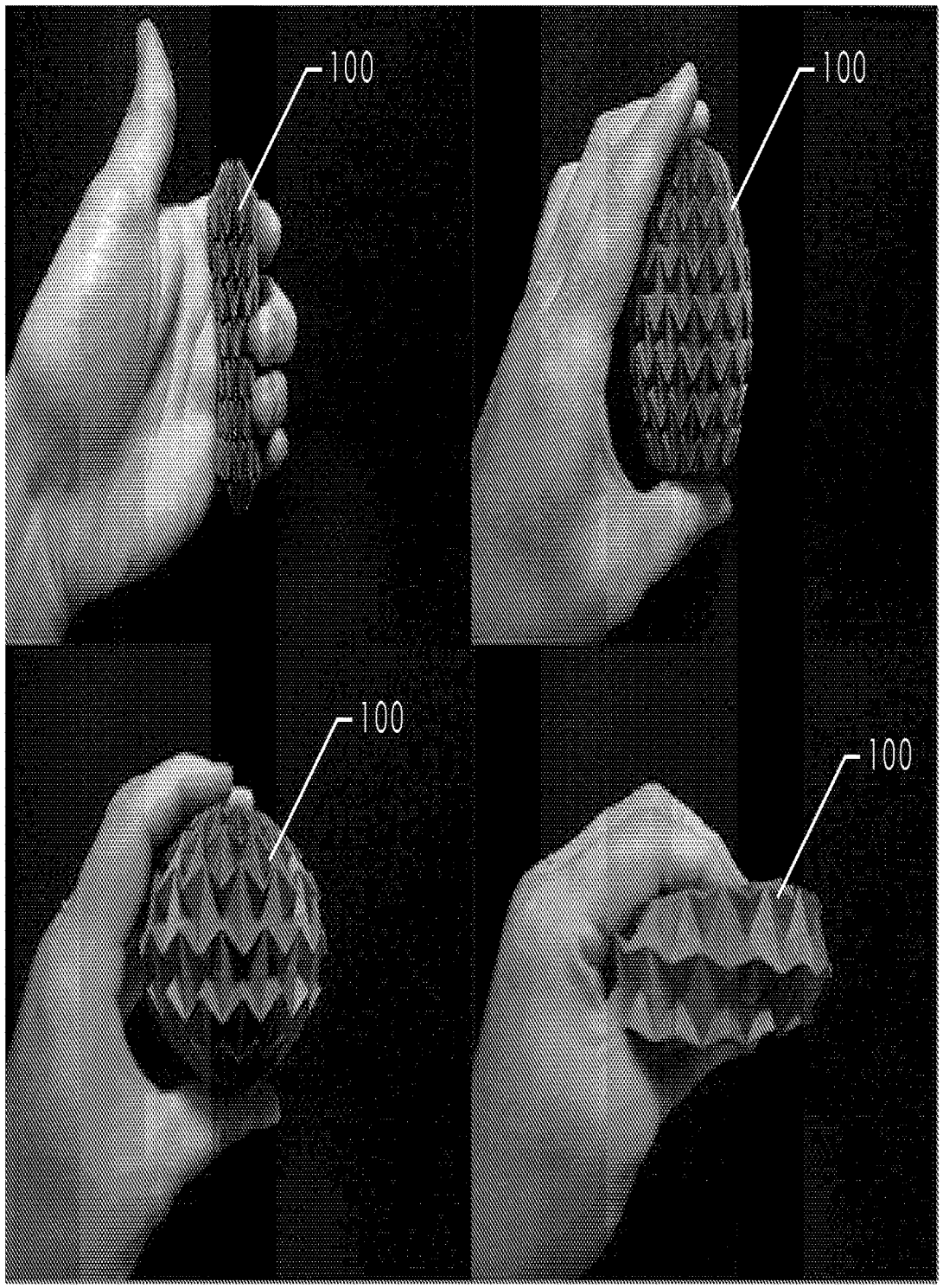
FIGS. 15A-D are photographs depicting an exemplary manner of folding and compressing a blockstent.
Figure 18:
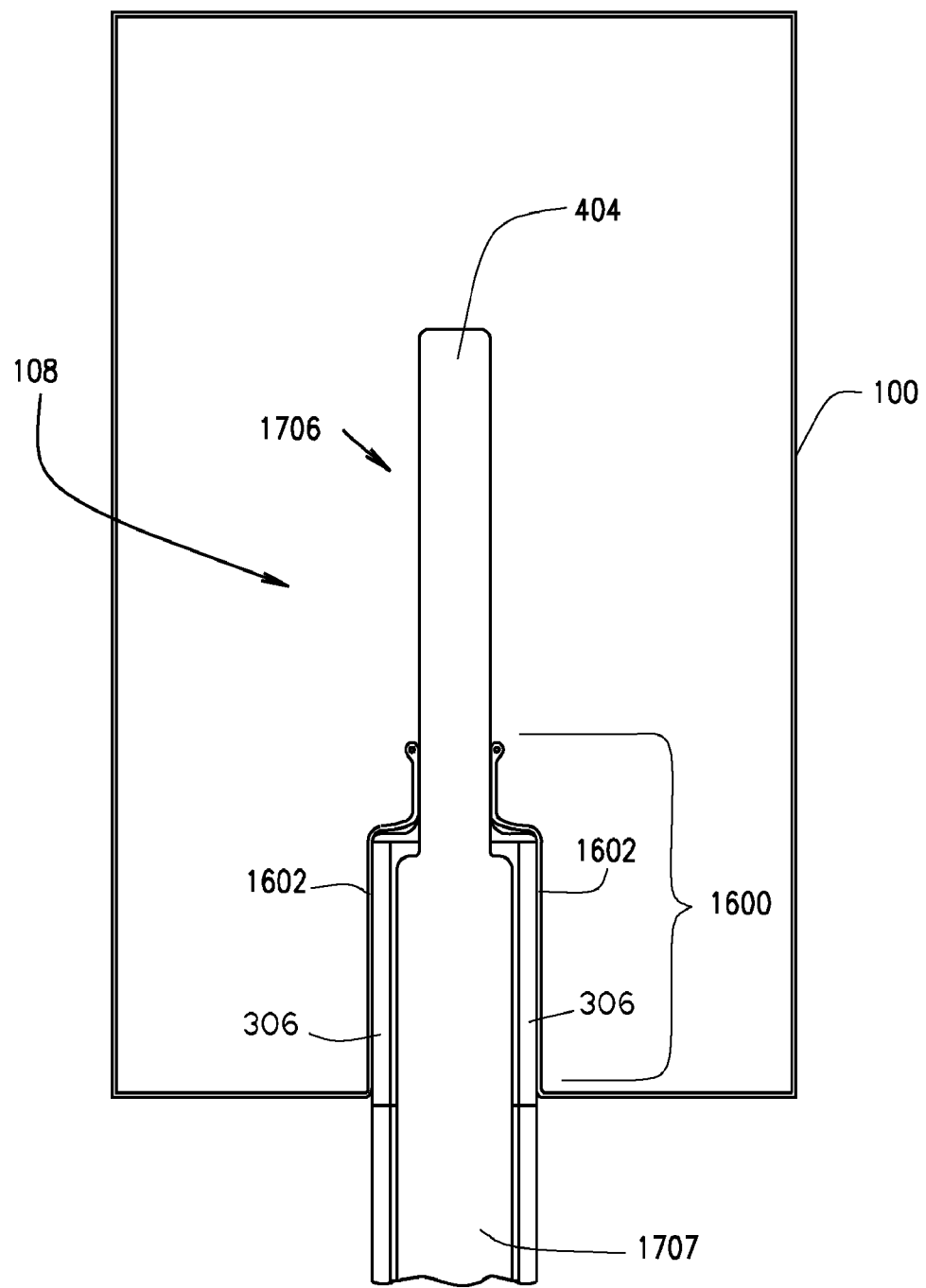
FIG. 18 depicts a hemispherical cross-sectional view taken along a diameter of an embodiment of the blockstent.

In FIG. 14A, the blockstent 100 has been pleated, folded, and wrapped around the shaft hollow cylindrical member 304 of the delivery catheter 2900, as shown in FIG. 14A. In FIG. 14B, the blockstent 100 has been similarly pleated and wrapped without the delivery catheter. In another embodiment, the blockstent 100 is folded into pleats, then the pleats of the folded blockstent are wrapped around the hollow cylindrical member 304 of the delivery catheter 2900, and the blockstent is compressed against the delivery catheter. In another embodiment, the blockstent 100 is folded into pleats, then the pleated folds of the folded blockstent are wrapped around the removable guide wire 302 or obturator 404, and then the blockstent is compressed against the removable wire or obturator 404. In another embodiment, the blockstent 100 is folded into pleats, and then the pleated folds are rolled into a generally cylindrical shape without a removable wire, obturator, or catheter acting as central fixation point.

In various embodiments, the blockstent 100 is attached to the delivery catheter 300, 400, then the pleats are formed, and then the pleated folds are wrapped and compressed onto the delivery catheter 300 or 2900, or the obturator 404. In another embodiment, the blockstent 100 is first folded to form pleats, then attached to the catheter 300, 400, and then the pleated folds are wrapped and compressed onto the outer surface of the delivery catheter 300, 2900, or obturator 404. In another embodiment, the blockstent 100 may be folded and compressed into a variety of shapes in a manner similar to Japanese origami, as shown in FIGS. 15A-D. [Nick—Do you want the origami pictures in Blockstent app?]

In various certain embodiments, the blockstent 100 need not be fully expanded to occlude a blood vessel segment. For example, the blockstent 100 may be partially expanded, or may be or completely expanded. In all embodiments, the blockstent remains in an expanded state (partially or completely) after detachment from the delivery catheter. An expanded state refers to the at least partial distention of the blockstent 100, such as at least 10%, 20%, 50%, 75%, or 90% and up to 100% of the maximum blockstent volume.

Blockstent Formation

The central layer 122 of the wall of the blockstent 102 and/or the interior and exterior layers 1400 and 104, respectively, may be formed by any suitable method. For example, in a preferred embodiment, the central layer 122 of the wall 102 is formed by electroforming or electroplating. A conductive mandrel is placed in a solution of metal ions, which coat the mandrel to form a layer of the blockstent 100. The shape of the blockstent 100 can be modified by modifying the shape of the mandrel. The thickness of the central layer 122 of the wall 102 can be modified by varying the process time. Regions of different wall thicknesses and the pattern of thickness differences may be produced by masking. In other exemplary methods of forming the blockstent 100, the central layer 122 of the wall 102 of the blockstent 100 may be formed by vapor deposition, wherein vapors from one or more polymers, pure metals, or metal alloys are condensed upon a substrate or mold (not shown). The mold may be removed to provide a hollow shell composed of the pure metal or metal alloy.

An exterior layer 104 may be formed on the outside of the central layer 122 of the blockstent 100 by additional electroplating or electroforming, by vapor deposition or by sputter deposition, wherein material is eroded from a target (e.g., a metal or metal alloy) and is then deposited onto a substrate (e.g., a mandrel or mold) forming a thin layer on the substrate.

An interior layer 1400 may be formed on the inside of the central layer 122 of the blockstent 100 by additional electroplating or electroforming, or by vapor deposition or by sputter deposition.

An exterior layer 104 may be formed on the outside of the central layer 122 of the blockstent 100 by additional vapor deposition. In some instances, the central layer 122 may be formed by electroforming or electroplating and the interior and exterior layers are formed by vapor deposition.

In some instances, it may be desirable to incorporate an elastomer layer into the blockstent 100, either as an interior or an exterior layer. In these instances, the elastomer can be added by incorporating a pre-formed material into the desired orientation, or by vapor deposition, or other methods.

The wall 102 of the main body of the blockstent 100 may be formed by different methods than the neck 116. The central layer 122 of the blockstent 100 may be formed by different methods than the exterior layer or coating 104 or the interior layer or coating 1400.

Two-dimensional sheets of metal may be manipulated and secured in the desired configuration to form the wall 102 and/or the exterior layer 104. These two dimensional sheets may further comprise rubber, plastic, polymer, woven or knitted fiber materials, or other materials, or combinations thereof. By way of example and not limitation, one or more two-dimensional sheets of a metal may be folded into a blockstent shape and welded, soldered, glued, or bonded together. Similarly, two-dimensional sheets of material may be manipulated and secured to form the exterior layer 104 or the interior layer 1400.

In various embodiments, a post forming wherein the wall 102 of the blockstent 100 comprises metal, an annealing process is used to improve ductility and facilitate folding, compressing, and/or expanding the blockstent 100. By way of example and not limitation, a typical annealing process includes heating the blockstent 100 at approximately 300° C. for a period of about one hour followed by an immediate quench in distilled water at room temperature.

The Delivery Catheter

The blockstent 100 is advanced and positioned within human body by an elongated portion of the medical device known as the "delivery catheter device". Typically, a delivery catheter device is an elongated surgical instrument that defines at least one lumen, or potential lumen, having a proximal and a distal end and that is dimensioned to deliver fluid from a fluid source at the proximal end into the central void or space 108 of the blockstent 100, which is attached to the distal end. Further, any medical device or component of a medical device that can position the blockstent 100 at a desired location in the vascular system, such as the lumen of a blood vessel segment, facilitate the expansion of the blockstent, and then facilitate the separation of the blockstent from the delivery device is generally acceptable as a delivery device. Typically, the delivery device is a catheter (a "delivery catheter"). Preferably, the delivery catheter may be any catheter, hollow wire, removable core wire, needle, trochar, other type of device, or combinations thereof, suitable for accessing locations with the vascular system, including the delivery catheters 300 and 400. The delivery catheter may also be any other type of catheter, hollow wire, or removable core wire, or alternatively a needle or trochar, or combinations thereof, suitable for accessing locations with the vascular system.

A catheter is a flexible, tubular, elongate medical device configured for insertion into bodily compartments, including blood vessels, to permit the injection or the withdrawal of fluids, amongst other functions. Catheters are often comprised of polymers or plastics and optionally further comprise metal, such as in a coil or braid configuration. Catheters can be configured to enable attachment to blockstents, facilitate the delivery of compressed blockstents to the lumen of a blood vessel, facilitate the expansion of compressed blockstents, and separate from expanded blockstents. The delivery catheter 300 or 400 can be configured to pass through the vascular system with the attached blockstent 100 in a compressed form, as shown in FIGS. 3A and 7A. After expansion, the blockstent 100 is separated from the catheter 300, thereby allowing the expanded blockstent to remain in place while the delivery catheter is removed from the body. In this way, delivery catheters are similar to angioplasty balloons, which are configured to enable attachment to traditional tubular stents, to facilitate the delivery of attached compressed traditional tubular stents to the lumen of a specific segment of a blood vessel, enable expansion of compressed traditional tubular stents, and separate from expanded traditional tubular stents.

Preferably, the delivery device is a catheter 400, as shown in FIG. 2 and FIG. 3A, which can carry an attached compressed blockstent 100 to the lumen of a blood vessel segment. The delivery catheter 400 is composed of a biocompatible material. By way of example and not limitation, the delivery catheter 300 and 400 and various components thereof may be composed of silicone rubber, natural rubber, polyvinyl chlorides, polyurethane, copolyester polymers, thermoplastic rubbers, silicone-polycarbonate copolymers, polyethylene ethyl-vinyl-acetate copolymers, woven polyester fibers, or combinations thereof. In one embodiment, the wall of the hollow cylindrical member, or delivery catheter 300 and 400, may be reinforced with a metal, such as coiled or braided stainless steel, nitinol or fibers, to enhance control and reduce kinking of the delivery catheter 300 and 400 during use. Metals suitable for delivery catheter reinforcement include stainless steel, nitinol or fibers.

As shown in FIGS. 2, 3A-B, 6, 7A-B and 16A-B, the delivery catheter 300 and 400 will have a hollow, or potentially hollow, cylindrical member that defines a lumen to allow for passage of fluid from the proximal end of the delivery catheter to the distal end of the delivery catheter and into the central void 108 of the blockstent. The delivery catheter 300 or 400 is designed and dimensioned such that it can be inserted in the body to deliver the compressed blockstent 100 to a desired location, facilitate the expansion of the blockstent, and facilitate the separation of the expanded blockstent from the delivery catheter. When a single lumen delivery catheter 400 is used, the compressed blockstent may be positioned in the lumen of a blood vessel segment after being advanced through a separate larger guide catheter that is positioned with its distal end within or near the blood vessel. Once in the lumen of the blood vessel and out of the guide catheter, the compressed blockstent 100 can be expanded, and then the expanded blockstent and the delivery catheter can be separated, and the delivery catheter and the guide catheter can be removed from the body, while the expanded blockstent remains in place. The hollow, or potentially hollow, cylindrical member 306 of delivery catheter 400 has a wall thickness ranging from about 0.05 mm to about 0.25 mm. Preferably, wall thickness of the hollow cylindrical member 306 ranges from about 0.1 mm to about 0.2 mm. The lumen 312 defined by the hollow cylindrical member 306 for the purpose of enabling the passage of fluid into the central void or space of the blockstent 108 has a diameter ranging from about 0.4 mm to about 1.0 mm. The proximal end of the hollow cylindrical member 306 includes a port or hub 308 or 406 to communicate with a pressurized fluid source, such as a syringe 314 or a pump (not shown) containing, for example, water, saline or a radiographic contrast solution. Fluids for expanding the blockstent are received into the delivery catheter 300 or 400 through the hub or port 308 or 406.

For some embodiments, the medical device is advanced in the body over a guidance member 302, as shown in FIG. 8B. Examples of a guidance member include a flexible guide wire. The guide wire 302 can comprise metal in the form of a flexible thread, coil, or slender rod. For example, the basic angiography guide wire consists of a fixed solid metal core covered by a metal spring coil. In other situations, a delivery catheter is advanced over a needle or trochar. The guide wire 302 occupies a lumen in the delivery catheter, with such lumen defined by the tubular portion of the delivery catheter. Once located in place, the guide wire 302 or trochar can be removed in order to allow the injection or withdrawal of fluids.

As shown in FIG. 6 and FIG. 16B, the delivery catheter 300 may include an additional hollow cylindrical member that defines a second lumen 324 to receive a guidance member, such as a guide wire 302, to assist in the guidance of the blockstent 100 component of the medical device to the desired location. This second lumen 324 is generally adjacent and parallel to the first lumen 312. As shown in FIG. 6 and FIG. 16B the delivery catheter may be a double lumen catheter, with one lumen 312 configured to enable the passage of fluid from a fluid source at the proximal end of the delivery catheter to the central void or space 108 of the blockstent at the distal end of the delivery catheter, and the other lumen 324 configured to accept a guidance member, such as a guide wire 302, to facilitate advancement and positioning of the medical device in the vascular system. As shown in FIG. 16B, the delivery catheter 300 includes two hollow cylindrical members, each with a lumen, wherein the hollow cylindrical members 304 or 306 have a wall thickness ranging from about 0.05 mm to about 0.25 mm. Preferably, the hollow cylindrical member 304 or 306 wall thickness ranges from about 0.1 mm to about 0.2 mm. The lumen defined by the hollow cylindrical member 304 for the accepting a guide wire 302 has a diameter ranging from about 0.25 mm to about 0.5 mm. The diameter of the lumen for the passage of fluid into the blockstent 312 and the diameter of the lumen for accepting a guidance member 324 may be similarly dimensioned. Alternatively, the diameter of the lumen for the passage of fluid into the blockstent may be larger or smaller than the diameter of the lumen for accepting a guidance member. For a delivery catheter with two lumens, the first and second hollow cylindrical members may be similarly dimensioned. Alternatively, the second hollow cylindrical member may have a larger diameter to accept the guidance member, or a smaller diameter. The proximal end of the second hollow cylindrical member 304 includes a guide wire port 310. The guide wire port 310 facilitates the insertion of the guide wire 302 into the second hollow cylindrical member 304. The guide wire 302 is fed through the second hollow cylindrical member 304 and extended out of the distal end of the delivery catheter 300. In this embodiment, the delivery catheter 300 is advanced over the guide wire 302 until the compressed blockstent 100 is positioned in the lumen of a blood vessel segment. Once the compressed blockstent 100 is in the desired position, the blockstent 100 is expanded by fluid provided to the first hollow cylindrical member 306 by the syringe 314 connected to the blockstent expansion port 308 or 406. Fluids such as saline, solutions of radiographic contrast agents, or solutions of drugs, such as thrombin, can be used to expand the compressed blockstent. The guide wire 302 is preferably an angiographic wire of sufficient length for the distal tip of the guide wire to reach the blood vessel, and a proximal end extending out and away from the point of entry into the vascular system. In some embodiments, the guide wire 302 has a straight or angled distal tip, while in other embodiments, the guide wire 302 has a curved J-shaped distal tip, typically constructed from a shape-memory alloy or a braided metal that causes the tip to return to the J-shape after any applied stress is removed. The materials and dimensions of the guide wire 302 may be selected based upon the diameter, length, and tortuosity of the blood vessels being traversed. Typically, the guide wire 302 may be composed of any suitable biocompatible materials and have an outer diameter ranging between 0.3 mm to 0.95 mm.

FIGS. 3A-B depict longitudinal views of a single lumen embodiment of the delivery catheter portion of the medical device 500. FIG. 3A depicts a longitudinal views of a single lumen embodiment of the medical device 500 with the blockstent in a compressed form. FIG. 3B depicts a longitudinal view of a single lumen embodiment of the medical device 500 with the blockstent in an expanded form. FIGS. 7A-B depict longitudinal views of a double lumen embodiment of the delivery catheter portion 300 of the medical device 500. FIG. 7A depicts a longitudinal view of a double lumen embodiment of the medical device 500 with the blockstent in a compressed form. FIG. 7B depicts a longitudinal view of a double lumen embodiment of the medical device 500 with the blockstent in an expanded form. As shown in FIGS. 8A-E, the delivery catheter 300 moves over the guide wire 302 to deliver the blockstent 100 to the lumen of a blood vessel segment 701, to deliver fluid to expand the blockstent in the blood vessel, and then separate therefrom. In certain embodiments, a modified infusion wire having a removable core can be used as a single lumen delivery catheter. An infusion wire is a modified guide wire wherein the solid metal core can be removed to leave a lumen that can be used to inject fluids. An infusion wire with a removable core can be modified such that a blockstent can be attached to the distal end and expanded through the wire lumen, after the removal of the core wire.

FIG. 2 depicts a longitudinal view of a single lumen embodiment of the delivery catheter portion 400 of the medical device 500. As shown in FIGS. 4A-E, for the single lumen embodiment, the delivery catheter 300 moves through the lumen of a guide catheter 800 to deliver the compressed blockstent 100 to the lumen 701 of a blood vessel segment 700. For this single lumen embodiment, the delivery catheter 400 does not include a hollow cylindrical member that defines a lumen that is dimensioned to allow for the passage of a guidance member, or guide wire.

FIG. 6 depicts a longitudinal view of a double lumen embodiment of the delivery catheter portion 300 of the medical device 500. As shown in FIGS. 8A-E, for the double lumen embodiment, the delivery catheter 300 moves over a guidance member or guide wire 302 to deliver the compressed blockstent 100 to the lumen 701 of a blood vessel segment 700.

As shown in FIGS. 17A-B, in another embodiment, the delivery catheter of the medical device can be configured with a lumen that can accept a guide catheter 800 as a guidance member. With this configuration, the medical device can be advanced in a tri-axial configuration, with the medical device 500 advanced over a guide catheter 800, which is advanced over a guide wire. In certain embodiments, the proximal hub on the guide catheter can be removed to allow the lumen of the hollow cylindrical member 304 of delivery catheter 300 of the medical device 500 to accept the guide catheter 800. In certain instances, this embodiment of the medical device can result in better control over the delivery of the compressed blockstent to the blood vessel and better trackability of the compressed blockstent 100 as it is advanced to the desired location. As shown, in one aspect, the hollow cylindrical member 304 of delivery catheter 300 may be annular shaped and fully encircle the guidance catheter 800, while in other aspects, the delivery catheter may engage 60%, 70%, 80%, 90% or more of the circumference of the guidance catheter.

The dimensions of the delivery catheter 300 or 400 are a matter of design choice depending upon the size of blood vessel to be treated and the location of the blood vessel in the vascular system. The distance between the blood vessel to be treated and the site of insertion of the delivery medical device into the vascular system, will determine, in part, the length of the delivery catheter 300 or 400. Delivery catheter lengths range between 5 cm and 300 cm, with preferable ranges between 75 cm and 225 cm. The smallest diameter blood vessel segment in the path between the site of insertion of the medical device into the vascular system and the blood vessel to be treated, will determine, in part, the diameter of the delivery catheter. Delivery catheter diameters range between 2 Fr and 7 Fr, with preferable ranges between 3 Fr and 5 Fr.

In some embodiments, the proximal end of the delivery catheter 400 is configured with a Luer hub or taper 406 or 308 that may facilitate a Luer-Lok™ or Luer-Slip™ type connection for connecting a fluid source, such as a syringe 314, to the lumen 312 of a hollow cylindrical member configured to transmit fluid from the proximal end of the delivery catheter to the central void or space of the blockstent 100. As shown, in FIG. 28, the lumen 312 of a delivery catheter 400 is connected to a fluid source, such as the syringe 314, through a female Luer fitting 2802. A stopcock 2804 may be positioned between the fluid source and the delivery catheter 400 to enable greater control over, the movement of fluid into and out of the delivery catheter.

Attaching the Blockstent to the Delivery Catheter and Separating the Expanded Blockstent from the Delivery Catheter The blockstent 100 may be attached to, or engaged with, the delivery catheter in a variety of ways. For example, the blockstent 100 may be affixed to the delivery catheter by a friction fit, using an adhesive or glue, by a weld or solder, by a junction or uniting of components, or by the application of a compressive force from a clamp, ring, elastomer sleeve or wrap, or compressive balloon. Various methods and devices may be used to separate the expanded blockstent from the delivery catheter. By way of example and not limitation, these methods and devices may be broadly categorized as physical or mechanical, electrical, thermal, chemical, hydraulic, and sonic.

In one embodiment, a physical or mechanical attachment is made between a blockstent and a delivery catheter, wherein the coupled parts are configured to fit tightly together and remain together by friction. After expansion of the blockstent, the physician slips the distal end of delivery catheter out of the neck of the blockstent to effect separation, a process that may be facilitated by moving a guide catheter 800 forward to abut the expanded blockstent 100 prior to withdrawing the delivery catheter as shown in FIG. 23B. For example, in one embodiment shown in FIG. 18, the neck 1600 of the blockstent 100 is inverted and located within the central void or space 108 of the blockstent. The exterior surface 1602 of the neck 1600 engages the distal end of the hollow cylindrical member 306 of the delivery catheter 400 by friction. When the blockstent 100 is compressed, it engages the distal end 1706 of the core wire or obturator 404 by friction. As shown in FIGS. 18, 22A-B, and 23A-B, the distal portion 1706 of the core wire or obturator 404 of the delivery catheter 400 has a smaller diameter than the more proximal portion 1707. In other embodiments, the distal portion 1706 of the core wire or obturator 404 of the delivery catheter 400 has the same diameter as the more proximal portion 1707. After the compressed blockstent 100 is positioned in the lumen of a blood vessel segment, the core wire or obturator 404 is removed. This creates a fluid pathway 1710 through the delivery catheter 400 to the central void or space 108 of the blockstent 100. Once the obturator 404 is removed, the blockstent 100 can be expanded. After the blockstent 100 is expanded, the distal end of the guide catheter 800 is advanced forward against the wall of the expanded blockstent 100 and the distal end of the delivery catheter 400 is withdrawn from the neck of the blockstent 1600 to separate the delivery catheter from the expanded blockstent, allowing the delivery catheter to be removed while leaving the expanded blockstent in the lumen of the blood vessel segment. In this way, the guide catheter 800 functions as a buttress against the exterior surface of the blockstent 112, while the expanded blockstent is separated from the delivery catheter. Alternatively, the blockstent and delivery catheter can be separated by other physical methods.

In another embodiment, a mechanical attachment is made between a blockstent and a delivery catheter wherein an external neck 1714 on the 110 blockstent is configured to fit tightly around the distal end of the hollow cylindrical member 306 of the delivery catheter 400. An elastic sleeve or wrap 1724 is attached to the distal end of the hollow cylindrical member 306 of the delivery catheter 400 and extended around at least a portion of the external neck of the blockstent 1714 of the blockstent 100 to hold the neck of the blockstent against the distal end of the hollow cylindrical member 306 of the delivery catheter 400, a configuration shown in FIG. 24. Once in place the blockstent is separated from distal end of the hollow cylindrical member 306 of the delivery catheter by using the guide catheter, similar to above, to buttress the blockstent while the distal end of the hollow cylindrical member 306 of the delivery catheter 400 is pulled away from the expanded blockstent.

In another embodiment, the blockstent 100 is attached to the distal end of the hollow cylindrical member 306 of the delivery catheter 300 or 400 with an adhesive, glue, weld, or solder. In this embodiment, the blockstent 100 is separated from delivery catheter 300 or 400 by mechanical methods.

The expanded blockstent 100 may be separated from the delivery device by a number of mechanical methods that cut, tear, or otherwise physically degrade a portion of the blockstent to separate the remainder of blockstent from the delivery catheter 300 or 400.

Figure 19:
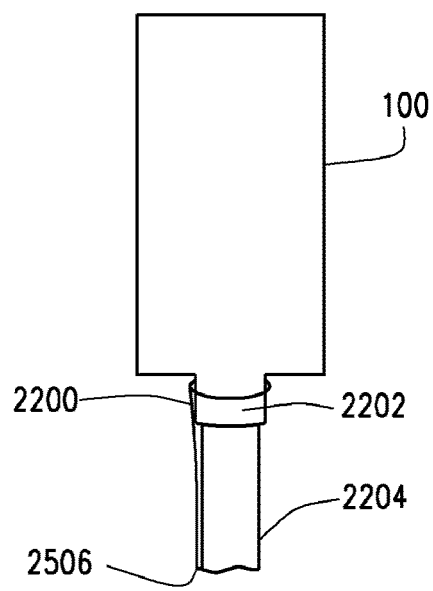
FIG. 19 is a plan view of a component and a method for separating a blockstent from a delivery catheter.

As shown in FIG. 19, in one embodiment, a flexible, thin loop of material 2200 may be positioned to encircle the outside of the external neck of the blockstent 116 or 2202. The loop of material can be comprised of various thin, strong, and flexible materials such as a wire, polymer strand, filament, string, thread, or snare. After expansion of the blockstent, the loop can be pulled toward the proximal end of the delivery catheter 2204 to sever the neck 116 or 2202 of the blockstent 100, and separate the expanded blockstent from the delivery catheter. Preferably, the loop is pulled through a lumen in the delivery catheter dimensioned to accept the loop as it is pulled back. In another embodiment (not shown), a flexible thin loop of material (in certain embodiments representing a loop snare or modified loop snare) can be advanced by a second catheter until the loop is placed around the outside of the proximal portion of the external neck of an expanded blockstent. The loop can then be snugged against the neck and withdrawn into the second catheter in order to sever the neck 116 of the blockstent 100 and separate the blockstent from the delivery catheter.

In another embodiment, shown in FIG. 19, a distal end 2500 of a thin loop of material (such as a wire, polymer strand, filament, string, or thread) is affixed in a loop to the blockstent neck 2202, while the proximal end 2506 of the loop material extends to the proximal end of the delivery catheter 2508. After expansion of the blockstent 100, the loop of material is pulled toward the proximal end of the delivery catheter 2204, which tears a portion of the neck 2202 away from the expanded blockstent 100 to separate the blockstent from the delivery catheter.

Figure 20A:
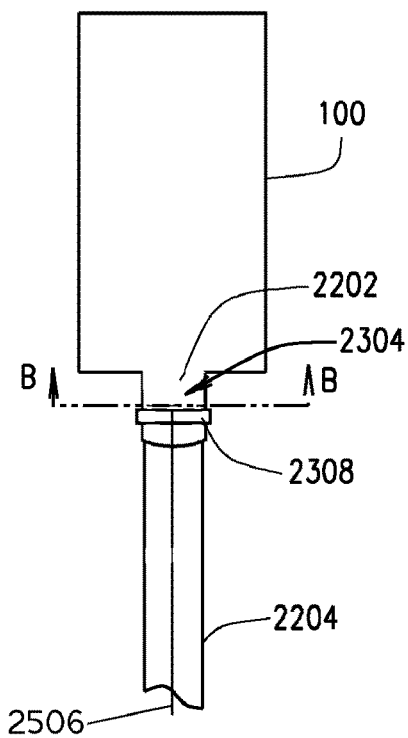
FIGS. 20A-C are plan views of a component and a method for separating a blockstent from a delivery catheter.
Figure 20B:
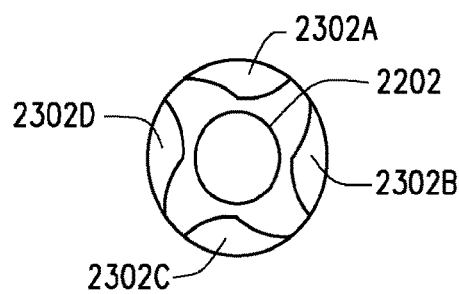
Figure 20C:
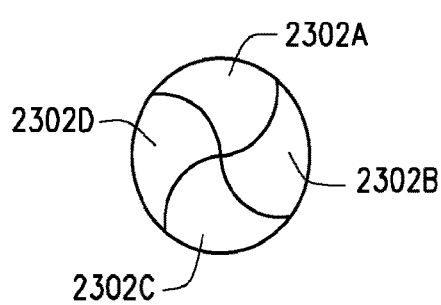

In another embodiment shown in FIGS. 20A-C, the neck 2202 of the blockstent 100 may be cut by one or more blades 2302A-D. In this embodiment, a cutting device 2304 is advanced over the delivery catheter 2204. The cutting device 2304 has a cutting region 2308 that includes the blades 2302A-D. When the expanded blockstent 100 is to be separated from the delivery catheter, the cutting device 2304 is positioned such that the neck 2202 is within the cutting region 2308. The blades 2302A-D may then be actuated to sever the neck 2202. By way of example and not limitation, the blades 2302A-D may be actuated by rotation of the cutting device, insertion of a wire, retraction of a wire, or other suitable methods. FIGS. 20B-C are cross-sectional views along line B-B of the cutting region prior to (FIG. 20B) and during actuation of the blades (FIG. 20C).

Figure 21:
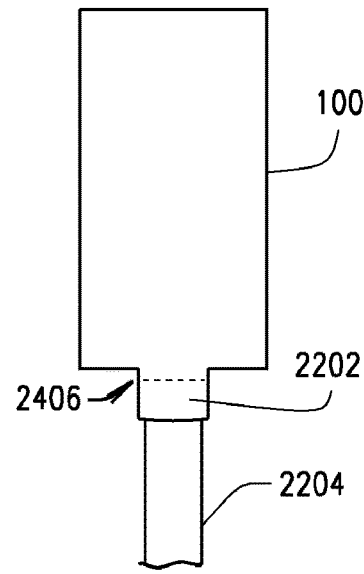
FIG. 21 is a plan view of a component and a method for separating a blockstent from a delivery catheter.
Figure 22B:
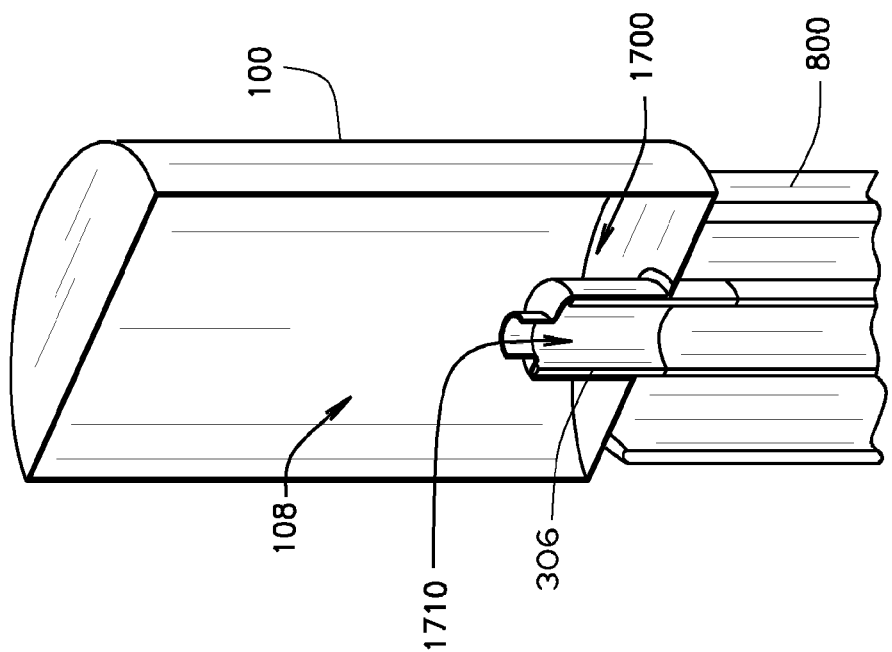
FIGS. 22A-B are perspective views of partial cross-sections of an embodiment of the medical device wherein the blockstent has an inverted, or internal, neck that is attached to the delivery catheter, wherein 22A depicts a compressed blockstent and 22B depicts and expended blockstent.
Figure 22A:
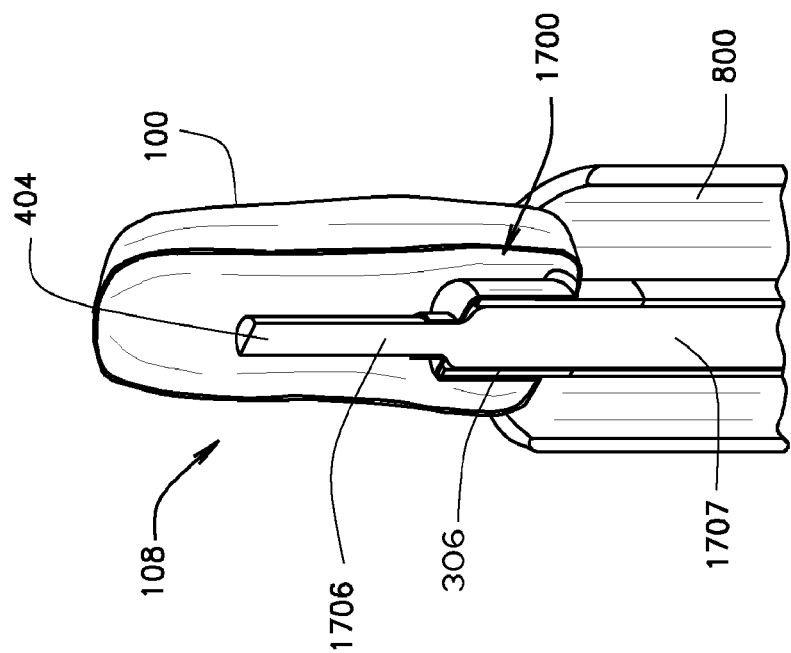

In another embodiment, shown in FIG. 21, the neck 2202 of the blockstent 100 may define a plurality of circumferential perforations 2406 that may be torn to separate the blockstent from the delivery catheter 2204.

In another embodiment, a ring structure is fixed to the distal end of the delivery catheter, while a second ring structure is fixed to the proximal end of the blockstent, with a mating of the two rings attaching the blockstent to the delivery catheter. After expansion of the blockstent, the rings can be disengaged, resulting in separation of the expanded blockstent 100 and the delivery catheter. The unlocking of the rings could be accomplished by actuating a spring-loaded clamp or other similar methods in order to release the blockstent.

In other embodiments, hydraulic methods may be used to separate the expanded blockstent 100 from the delivery catheter device. In one embodiment, the expanded blockstent 100 separates from the delivery catheter after fluid is injected through a lumen to actuate a mechanical joint between the blockstent 100 and the delivery catheter, resulting in separation of the expanded blockstent 100 and the delivery catheter.

In one embodiment, a mechanical attachment is made between a blockstent and a delivery catheter wherein a portion of the blockstent is attached to the distal portion of the delivery catheter using one or more welds or solder 316 that are not insulated, and sensitive to electrolysis. For this embodiment, an insulated conductor wire or an electrolysis wire 320 extends along the length of the delivery catheter from the proximal end of the delivery catheter 300 or 400. The electrolysis wire 320 or an insulated conductor wire can electrically couple a source of electrical current outside the patient's body, to the distal portion of the delivery catheter where it is coupled to the weld or solder that attaches the blockstent to the delivery catheter. In this way, the electrolysis wire 320 or the insulated conductor wire is in electrical communication with the weld or solder that attaches the blockstent to the delivery catheter. In various embodiments, the electrolysis wire 320 or the insulated conductor wire or the electrolysis wire 320 can lie within the wall of the delivery catheter 300 or 400, along the exterior surface of the delivery catheter, or within a lumen of the delivery catheter. The electrolysis wire 320 or the insulated conductor wire is in electrical communication with the weld or solder between the blockstent and the delivery catheter. In some embodiments, the electrolysis wire 320 is insulated, wherein the weld or solder is not insulated. In other embodiments, the electrolysis wire 320 and the weld or solder 316 is not insulated, but a portion of the blockstent 100 is not insulated. In some embodiments, the electrolysis wire 320 and the blockstent 100 are insulated, while the weld or solder 316 is not insulated. An electrical current or charge is applied to the electrolysis wire 320 or the insulated conductor wire after the blockstent 100 is expanded. The current is applied in an amount and for a time sufficient to dissolve at least a portion of the weld or solder and separate the delivery catheter from the blockstent 100, leaving the blockstent expanded at the desired position while the delivery catheter is removed. In one embodiment the current is applied in an amount and for a time sufficient to dissolve at least a portion of the blockstent and separate the delivery catheter from the blockstent 100, leaving the blockstent expanded at the desired position while the delivery catheter is removed. In one embodiment the current is a direct current (DC) while in another embodiment, the current is an alternating current (AC). The electrolysis wire 320 or the insulated conductor wire is in electrical communication with the weld or solder 316. In this embodiment, a DC current is applied to the electrolysis wire 320 or the insulated conductor wire after the blockstent 100 is expanded. The DC current dissolves at least a portion of the weld or solder 316, resulting in separation of the blockstent 100 and the delivery catheter, and leaving the blockstent 100 expanded at the desired position while the delivery catheter is removed.

Figure 28:
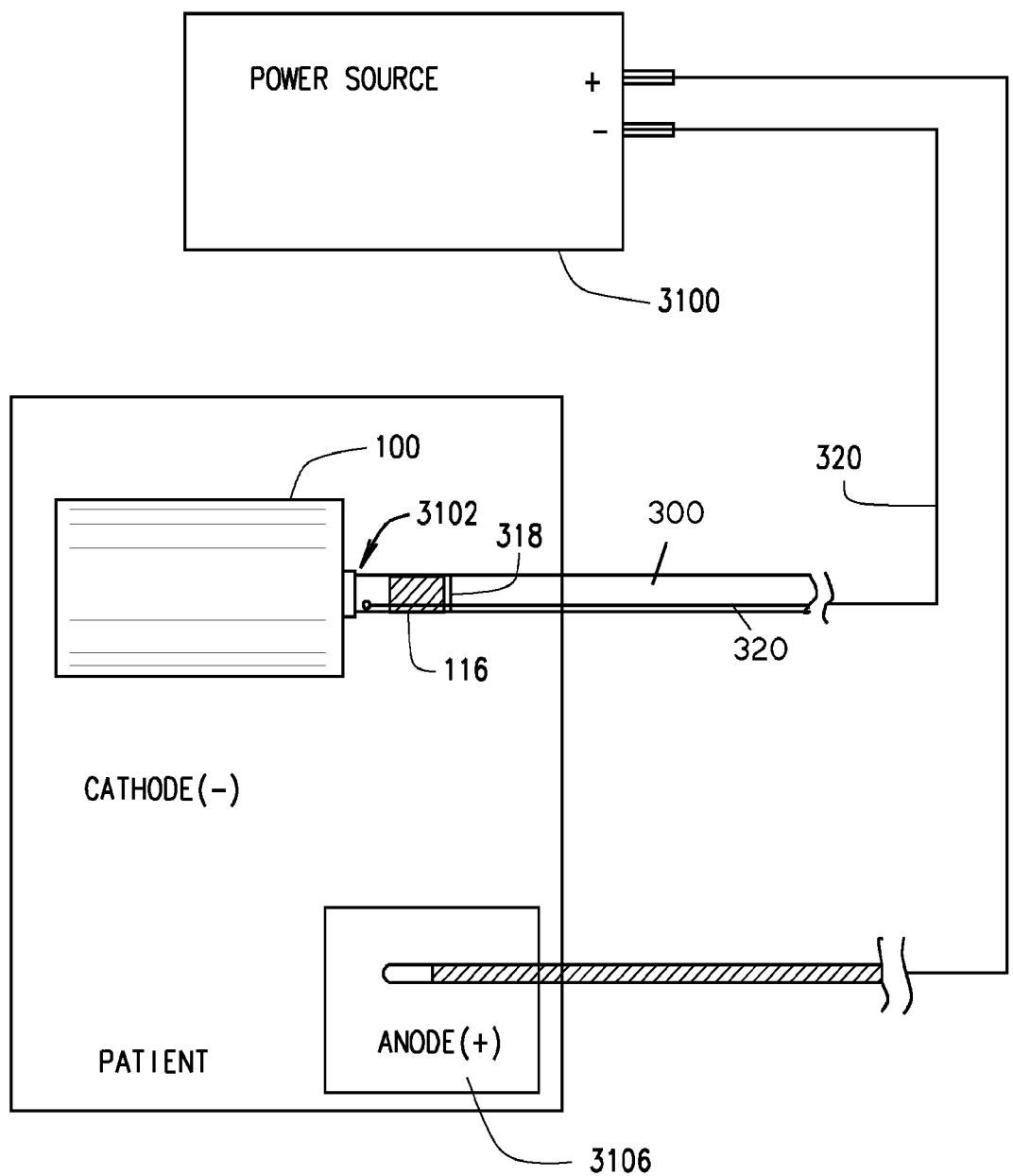
FIG. 28 is a plan view of an embodiment of the medical device wherein the blockstent is attached to the delivery catheter with an adhesive and separated from the delivery catheter by electrolysis.

FIG. 28 depicts another embodiment for separating an expanded blockstent and the delivery catheter by electrolysis. For this embodiment, a portion of the blockstent 100 is affixed to the delivery catheter 400 by an adhesive 318. An electrolysis wire 320 or an insulated conducting wire extends along the length of the delivery catheter from the proximal end of the delivery catheter 400, where it can be coupled to a power source or sources of electrical current 3100 outside the patient's body, to the distal portion of the delivery catheter where it is coupled to the proximal portion of the blockstent 100. In this way, the electrolysis wire 320 or insulated conducting wire is in electrical communication with the portion 3102 of the blockstent that is not insulted 3102 and that is not bonded to the delivery catheter. In various embodiments, the electrolysis wire 320 or insulated conductor wire can lie within the wall of the delivery catheter 400, along the exterior surface of the delivery catheter, or within a lumen of the delivery catheter. In another embodiment, the insulated conductor wire or the electrolysis wire 320 is in electrical communication with the proximal portion of the blockstent 3102. In some embodiments, the electrolysis wire 320 is insulated, wherein a proximal portion 3102 of the blockstent 100 is not insulated. In some embodiments, the electrolysis wire 320 and the remainder of the blockstent 100 and 116 are insulated, while a proximal portion 3102 of the blockstent 100 is not insulated. An electrical current or charge is applied to the electrolysis wire 320 or insulated conductor wire after the blockstent 100 is expanded. The current is applied in an amount and for a time sufficient to dissolve at least a portion of the non-insulated portion of the blockstent 3102, resulting separation the delivery catheter from the blockstent 100, leaving the blockstent expanded at the desired position while the delivery catheter is removed. In one embodiment the current is a direct current (DC) while in another embodiment, the current is an alternating current (AC). In this embodiment, a DC current is applied to the insulated conductor wire or electrolysis wire 320 after the blockstent 100 is expanded. The blockstent 100 functions as a cathode, while a grounding pad 3106 functions as an anode. The DC current dissolves at least a portion of the non-insulated portion 3102 of the blockstent 100, resulting in separation of the blockstent 100 and the delivery catheter, and leaving the blockstent 100 expanded at the desired position while the delivery catheter is removed. In one embodiment, the exterior, the interior, or both of the blockstent neck 116 may be coated with an insulating substance, such as a polymer including but not limited to Parylene™. In another embodiment, the exterior, the interior, or both of the blockstent neck 116 and the blockstent (except for portion 3102) may be coated with an insulating substance, such as a polymer including but not limited to Parylene™. The electrolysis wire 320 or the insulated conductor wire is then brought into physical contact, or otherwise electrically coupled with a portion 3102 of the neck 116 that is uncoated and not otherwise insulated. The uncoated portion 3102 of the neck 116 may be intentionally left uncoated during the coating process or may be exposed after coating by laser etching or ablation, as with a laser, or other suitable processes. The remainder of the blockstent may be coated and insulated (inside surface, outside surface, or both surfaces) to reduce the time required to dissolve the portion 3102 of the blockstent that is not coated or insulated.

In another embodiment, as shown in FIGS. 25A-B, a mechanical attachment is made between a blockstent and a delivery catheter wherein a portion of the blockstent is attached to the distal portion of the delivery catheter using one or more bonds that are sensitive to an adhesive or binding agent 2700 that melts with heating, such as with a low melting temperature binding agent applied between the hollow cylindrical member 306 of the delivery catheter and the blockstent. After expansion of the blockstent, an electrical current is passed through the bond, generating heat by using a resistance heating element 2702 in electrical communication with a conduction wire 2704, as shown resulting in warming of the adhesive or binding agent. As the binding agent 2700 is melted, the blockstent 100 is separated from the delivery catheter 2706. The binding agent 2700 may be metal (e.g. gold foil) or a polymer binding agent that is positioned at the neck of the blockstent.

In another embodiment, a mechanical attachment is made between a blockstent and a delivery catheter wherein a portion of the blockstent is attached to the distal portion of the delivery catheter using one or more bonds that are sensitive to chemical dissolution. The bonding medium may be composed such that the bonding medium dissolves when contacted by a solution with a high salt concentration, an acid, a base, or a specific chemical. By way of example and not limitation, a cover or other shielding device may be removed from the region where the blockstent 100 is joined to the delivery catheter to expose the bonding medium. Also by way of example and not limitation, injection or infusion of a solution with a high salt concentration, an acid, a base, or a specific chemical to the region of the bonding, after expansion of the blockstent at the desire location can result in dissolution of the bonding medium and separation of the expanded blockstent and the delivery catheter.

In another embodiment, a mechanical attachment is made between a blockstent and a delivery catheter wherein a portion of the blockstent is attached to the distal portion of the delivery catheter using one or more adhesives, glues, bonds, welds, or solder that are sensitive to sonic waves. In this embodiment, the bond between the blockstent 100 and the delivery catheter is broken using sound waves, such as focusing pulsed ultrasound waves, resulting in separation of the delivery catheter and the expanded blockstent.

In one embodiment, the wall opening of the expanded blockstent 100 is left open at the end of the procedure. In other embodiments, the wall opening of the expanded blockstent 100 is closed prior to the end of the procedure. By way of example and not limitation, an opening may be sealed by applying an external force, such as with the inflation of the balloon portion of a balloon catheter adjacent to the expanded blockstent. Alternatively, an opening may be sealed by snugging a loop of flexible material around the external surface of the neck of the blockstent 100 prior to separation of the expanded blockstent and the delivery catheter. In this method, the loop of material may comprise a wire, polymer strand, filament, string, thread, or snare.

In all embodiments, the blockstent 100 retains its expanded shape after detachment and is resistant to compression. The blockstent 100 remains expanded even if the pressures inside and outside of the expanded blockstent are equal or similar because of the rigidity of the wall of the blockstent. In another example, maintenance of the blockstent expansion is assisted by placing rigid, semi-rigid, or expansile materials into the blockstent 100 as needed. Examples of these materials include metallic or polymeric coils, metallic or polymeric expansile structures, beads, balls, spheres, or microspheres.

According to any of the methods where the blockstent 100 is separated from delivery catheter, one or more radiopaque markers may be incorporated into the appropriate portions of the blockstent or delivery catheter to assist in the positioning of the blockstent, expansion of the blockstent, separation of the expanded blockstent from the delivery catheter, and removal of the delivery catheter after separation. For example, a radiopaque marker band or spot may be incorporated into the medical device to identify the location where separation is designed intended to occur. In addition, radiopaque material may be incorporated into the blockstent. Also, a radiopaque spot or marker band or spot may be incorporated into distal end of the delivery catheter so that the tip of the delivery catheter can be seen under fluoroscopy while pulling the delivery catheter away from the expanded blockstent. A radiopaque marker may also be placed onto the detachment components, as need be. The radiopaque spot or marker band may be comprised of various radiodense materials, including but not limited to a metal band, a metal spot or line, or a line of barium.

Methods of Use

Methods of the present invention generally include placing a compressed blockstent 100 into the lumen 701 of a blood vessel segment 700 using a delivery catheter 300 or 400 and expanding it to fill all or a substantial portion of the lumen of the blood vessel, thereby occluding it. As part of the method, the delivery device can be positioned using a guide catheter 800 or guide wire 302, which have been placed in or near the blood vessel 700. Once the blockstent 100 is expanded, the delivery catheter 300 or 400 is separated from the blockstent, which remains in the lumen 701 of the blood vessel 700 in an expanded state. Attaching of the blockstent 100 to the delivery catheter 300 or 400 and separation of the expanded blockstent and the delivery catheter can be accomplished via a variety of methods, as disclosed herein.

The shape of a blockstent 100 that has been expanded in the lumen of a blood vessel segment is determined, in part, by the formed shape of the blockstent. For example, in some embodiments, the blockstent 100 is manufactured into a cylindrical, oblong, irregular, or non-spherical orientation to match the contours of the cavity for a particular blood vessel segment 700. The expanded shape is also determined by the size and shape of the lumen of the blood vessel segment. The expanded shape can also be determined by the application of an external force, such by inflating the balloon portion of a balloon catheter adjacent to the expanded blockstent. In certain embodiments of the methods, the balloon portion 1102 of a balloon catheter 1100 is inflated in the lumen of the parent blood vessel 1202 adjacent to the expanded blockstent 100 in the lumen of the blood vessel, thereby pushing the wall 1104 of the blockstent 100 toward the blood vessel. In other embodiments, the blockstent 100 is manufactured into a non-spherical orientation to match the contours of the cavity for a particular blood vessel segment 700.

In all embodiments, the expanded shape of the blockstent 100 is determined by these factors: 1) the manufactured shape of the blockstent 100; 2) the degree of blockstent expansion; 3) the size and shape of the blood vessel 700; and 4) the effect of any applied external force on the blockstent after expansion. By way of example and not limitation, the manufactured size and shape of the blockstent 100 may be determined by making measurements of the blood vessel 700. The measurements can be made by using medical images, including two dimensional and three dimensional reconstructions, and standard distance reference markers. Other methods of measuring the blood vessel may also be used.

In another embodiment, the blockstent 100 may position, size, and shape of the expanded blockstent can be manipulated and configured in vivo or even in situ while positioned within the blood vessel 700. In this embodiment, it is not necessary to determine the precise contours of the blood vessel 700 prior to inserting the blockstent 100. The blockstent 100 is shaped by the degree of expansion of the blockstent and the application of internal and/or external forces. For example, an external force may be applied by inflating the balloon portion of a balloon catheter adjacent to the expanded blockstent, or by tools inserted through or around the delivery catheter 400 or guide catheter 800. In other embodiments, the blockstent 100 may be shaped in a step prior to or after the step of separating the expanded blockstent from the delivery catheter 400.

In embodiments, the blockstent is designed so that the exterior surface 110 of the expanded blockstent 100 makes contact with a substantial portion of the inner surface 704 of the blood vessel 700. In some embodiment, the exterior surface 110 of the blockstent 100 makes contact with at least 50%, 75%, 90% or more of the inner surface 704 of the blood vessel 700 including up to 100%. In embodiments, the expanded blockstent is designed to fill the lumen of the blood vessel 701. In one embodiment, the expanded blockstent 110 fills at least 50%, 75%, 90% or more of the volume of the lumen 701 of the blood vessel 700 including up to 100%.

In all embodiments, the blockstents are configured to maintain their expanded shapes and expanded blockstents are not designed for, or intended to be, compressed or flattened into disc-like structures before or after separation from the delivery catheter.

By way of example and not limitation, a method of using the device 500 to treat a patient may include the steps of examining a patient and collecting diagnostic medical images to identify a blood vessel segment. The vascular system may be accessed using any suitable method including accessing an artery or vein using the Seldinger technique. A guide wire 302 is then inserted into the vascular system. Then a guide catheter 800 is inserted into the vascular system and advanced into or near the lumen of the blood vessel segment. The blood vessel is visualized by use of an injected radiopaque dye. The guide wire 302 is removed and the medical device 500 is then inserted through the guide catheter 800 until the compressed blockstent is advanced into the lumen 701 of the blood vessel 700. The blockstent 100 is then expanded in the lumen 701 of the blood vessel 700. A radiographic contrast solution may be injected into the adjacent vessel 1202 near the blood vessel 700 to confirm that the size of the expanded blockstent 100 is appropriate and that it is properly positioned in blood vessel. Once proper placement and sizing of the expanded blockstent 100 has been confirmed, the expanded blockstent is separated from the delivery catheter 300 or 400 by any of the methods disclosed herein, and the delivery catheter is removed. The expanded blockstent 100 is left in the patient, where subsequent examination may be conducted to determine if additional treatment is necessary. The expanded blockstent 100 left in the patient functions to prevent bleeding or expansion of the blood vessel and it alleviates future medical problems the patient might experience had the blood vessel 700 not been treated.

By way of example and not limitation, a method of using the device 500 to treat a patient may include the steps of examining a patient and collecting diagnostic medical images to identify a blood vessel segment. The vascular system may be accessed using any suitable method including accessing an artery or vein using the Seldinger technique. A guide wire 302 is then inserted into the vascular system. Then a guide catheter 800 is inserted into the vascular system and advanced with the guide wire 302 until the guide wire 302 is positioned in or near the lumen of the blood vessel segment. The blood vessel 700 is visualized by use of an injected radiopaque dye. The guide catheter 800 is removed and the medical device 500 is then inserted over the guide wire until the compressed blockstent 100 is advanced into the lumen 701 of the blood vessel 700. The guide wire 302 is removed. The blockstent is expanded 100 in the lumen 701 of the blood vessel 700. A contrast solution may be injected into the adjacent vessel 1202 near the blood vessel 700 to confirm that the size of the blockstent 100 is appropriate and that it is properly positioned in the vessel, and that the treated vessel is occluded. Once proper placement and sizing of the expanded blockstent 100 has been confirmed, the expanded blockstent is separated from the delivery catheter 300 or 400 by any of the methods disclosed herein and the delivery catheter is removed. The expanded blockstent 100 is left in the patient, where subsequent examination may be conducted to determine if additional treatment is necessary.

In various embodiments, a medical kit may be provided for treating a patient with the medical device. The medical kit may include the medical device 500, a guide wire 302, one or more guide catheters 800, one or more blockstent support structures and methods for separating the expanded blockstent 100 from the delivery catheter 300 or 400 including separate medical devices for separation, components of the medical device 500 for separation, and methods of use. The medical kit may further include instructions for use.

Two or more blockstents 100A-B may be used in combination to fill the lumen or void 701 of the blood vessel 700, as illustrated in FIG. 26. Additionally, a second, third, or more blockstents may be required to fill the remaining portion of the blood vessel not filled by the first blockstent.

It will be appreciated that the devices and methods of the present invention are capable of being incorporated in the form of a variety of embodiments, only a few of which have been illustrated and described above. The disclosures herein may be embodied in other specific forms without departing from its spirit or essential characteristics. The described embodiments are to be considered in all respects only as illustrative and not restrictive and the scope of the present invention is, therefore indicated by the appended claims rather than by the foregoing description. All changes that come within the meaning and range of equivalency of the claims are to be embraced within their scope.

What is claimed is:

1. A medical device for occluding an artery or a vein, the medical device comprising:
   a catheter that includes a first cylindrical member that defines a first lumen and a second cylindrical member that defines a second lumen;
   a compressed, hollow metal structure comprised primarily of gold, wherein the hollow gold structure, when expanded, assumes a generally cylindrical form, comprises a single lobe having a wall with an interior surface defining a void, and an exterior surface, with an opening in the wall that allows for the passage of fluid from the first lumen into the void, wherein the void of the hollow gold structure and the first lumen of the catheter are fluidly connected;
   wherein the catheter is dimensioned to deliver fluid from a fluid source at the proximal end through the first lumen and into the void of a hollow gold structure at the distal end;
   wherein the catheter is dimensioned to allow for the passage of a guidance member, or guide wire, through the second lumen defined by the second cylindrical member, wherein the second lumen passes entirely through the hollow gold structure;
   wherein the hollow gold structure is folded to form one or more pleats and the pleats are compressed against at least a portion of the catheter;
   wherein the passage of fluid from the catheter into the void of the compressed hollow gold structure results in expansion of the hollow gold structure;
   wherein the medical device is configured such that the expanded hollow gold structure and the catheter can be separated; and
   wherein the expanded hollow gold structure has sufficient rigidity to remain in an expanded state when implanted in vivo in an unsealed configuration.

2. The medical device of claim 1, wherein the hollow gold structure comprises a polymer layer or coating.

3. The medical device of claim 2, wherein the thickness of the polymer or coating is between 0.1 µm and 59 µm.

4. The medical device of claim 2, wherein the total thickness of the wall is between 2 µm and 60 µm.

5. The medical device of claim 2, wherein the polymer layer or coating is external to the gold layer.

6. The medical device of claim 2, wherein the polymer layer or coating is internal to the gold layer.

7. The medical device of claim 2 wherein the polymer layer or coating is configured to reduce the leaking of fluid from the hollow metal structure during expansion.

8. The medical device of claim 7 wherein the polymer layer or coating is a continuous layer.

9. The medical device of claim 1, wherein the thickness of the gold layer is between 5 µm and 20 µm.

10. The medical device of claim 1, wherein the hollow gold structure has an expanded diameter of 2 mm to 30 mm.

11. The medical device of claim 1, wherein the hollow gold structure has an expanded length of 5 mm to 60 mm.

12. The medical device of claim 1, wherein the exterior surface of the hollow gold structure comprises microscopic projections.

13. The medical device of claim 12, wherein the projections range in length from 0.01 µm to 57 µm.

14. The medical device of claim 1, wherein the exterior surface of the hollow gold structure is porous.

15. The medical device of claim 14, wherein the pores have a diameter of 0.01 µm to 0.5 µm.

16. The medical device of claim 1, wherein the hollow gold structure comprises one or both of a proximal neck and a distal neck.

17. The medical device of claim 16, wherein the hollow gold structure comprises both a proximal neck and a distal neck and both the proximal neck and the distal neck of the hollow gold structure project away from the body of the hollow gold structure.

18. The medical device of claim 17, wherein the proximal neck of the hollow gold structure is formed by different methods than the body.

19. The medical device of claim 16, wherein at least one of the proximal neck or the distal neck of the hollow gold structure is configured to close and form a seal after separation from the catheter to assume a sealed configuration.

20. The medical device of claim 19, wherein the distal neck of the hollow gold structure is configured to close and form a seal after separation from the catheter to assume a sealed configuration.

21. The medical device of claim 16, wherein after separation from the catheter, one of the proximal neck or the distal neck is sealed and the other neck remains open after withdrawal of the catheter, to assume a partially sealed configuration.

22. The medical device of claim 1, wherein a portion of the wall of the hollow gold structure is formed by electroforming.

23. The medical device of claim 1, wherein the central layer of the hollow gold structure is formed by different methods than the exterior layer or coating, or the interior layer or coating.

24. The medical device of claim 1, wherein the hollow gold structure comprises an outer layer comprising gold and an inner layer comprising a polymer and wherein the gold layer and the polymer layer are bonded together.

25. The medical device of claim 1, wherein the hollow gold structure is annealed.

26. The medical device of claim 1, wherein the diameter of the catheter and the compressed hollow metal structure prior to expansion is 2-5 Fr.

27. The medical device of claim 1, wherein the wall of the catheter is reinforced with wound or braided wire.

28. The medical device of claim 27, wherein the wire is comprised of stainless steel or nitinol.

29. The medical device of claim 1, wherein the length of the catheter is 75-225 cm.

30. The medical device of claim 1, wherein a radiopaque marker band or spot is incorporated into the medical device to identify the location where separation of the hollow gold structure and the catheter is designed to occur.

31. The medical device of claim 1, wherein a radiopaque marker band or spot is incorporated into the medical device to identify the distal end of the catheter.

32. The medical device of claim 1, wherein the compressed hollow gold structure can be expanded by injection of a fluid comprising water or saline into the void of the hollow gold structure at a pressure less than 5 atmospheres.

33. The medical device of claim 1, wherein the hollow gold structure and the catheter are coupled by friction, without an adhesive bond, solder, or weld.

34. The medical device of claim 33, wherein:
the proximal neck of the hollow gold structure projects away from the body and is configured to fit around the distal end of the catheter; and
an elastic sleeve or wrap is extended around at least a portion of the proximal neck of the hollow gold structure to hold the proximal neck of the hollow gold structure against the distal end of the catheter.

35. The medical device of claim 34, wherein the elastic sleeve or wrap is attached to the distal end of the catheter.

36. The medical device of claim 33, wherein the expanded hollow gold structure and the catheter can be pulled apart by withdrawing the catheter while the expanded hollow gold structure is held in place.

37. The medical device of claim 1, wherein the expanded hollow gold structure and the catheter can be pulled apart by withdrawing the catheter while the expanded hollow gold structure is held in place.

38. The medical device of claim 1, wherein the expanded hollow gold structure is supported by a rigid or semi rigid material inside the void of the expanded hollow gold structure.

39. The medical device of claim 1, wherein the expanded hollow gold structure is not supported by a rigid or semi rigid material inside the void of the expanded hollow gold structure.

* * * * *